(12) United States Patent
Radl et al.

(10) Patent No.: US 10,405,877 B2
(45) Date of Patent: Sep. 10, 2019

(54) EXCISING INSTRUMENT, SYSTEM INCLUDING THE SAME, AND METHOD FOR REMOVING A TISSUE SPECIMEN OR ORGAN WITHIN A FLEXIBLE POUCH EXTENDING THROUGH A SMALL INCISION OR NATURAL OPENING IN A PATIENT

(71) Applicant: Boehringer Technologies, LP, Phoenixville, PA (US)

(72) Inventors: Christopher L. Radl, Malvern, PA (US); Allison Lloyd Lehmann, Norristown, PA (US); Kevin P. Klocek, Wynnewood, PA (US); Trevor Smith, Round Lake Beach, IL (US)

(73) Assignee: Boehringer Technologies, LP, Phoenixville, PA (US)

( * ) Notice: Subject to any disclaimer, the term of this patent is extended or adjusted under 35 U.S.C. 154(b) by 289 days.

(21) Appl. No.: 15/429,879

(22) Filed: Feb. 10, 2017

(65) Prior Publication Data

US 2017/0311971 A1    Nov. 2, 2017

Related U.S. Application Data

(60) Provisional application No. 62/329,414, filed on Apr. 29, 2016, provisional application No. 62/422,402, filed on Nov. 15, 2016.

(51) Int. Cl.
*A61B 17/3205* (2006.01)
*A61B 17/00* (2006.01)
(Continued)

(52) U.S. Cl.
CPC .... *A61B 17/3205* (2013.01); *A61B 17/00234* (2013.01); *A61B 17/32002* (2013.01);
(Continued)

(58) Field of Classification Search
CPC .............. A61B 17/42; A61B 17/00234; A61B 17/32002; A61B 17/3205
See application file for complete search history.

(56) References Cited

U.S. PATENT DOCUMENTS 5,215,521 A    6/1993  Cochran et al.
5,320,627 A *  6/1994  Sorensen ......... A61B 17/00234
                                                600/564
(Continued)

FOREIGN PATENT DOCUMENTS

WO    2015164591 A1    10/2015

OTHER PUBLICATIONS

International Search Report for PCT/US2017/029359 dated Jul. 6, 2017.

*Primary Examiner* — Tuan V Nguyen
(74) *Attorney, Agent, or Firm* — Caesar Rivise, PC

(57) ABSTRACT

A system and method for removing a tissue specimen or organ from the body of patient is disclosed. The system includes a bag and an excising instrument. The tissue specimen or organ is located in the bag, which is located in the patient's body. The instrument comprises a guide and a cutter. The guide is configured for introduction into the bag. The cutter is rotatable within the guide and includes a central passageway and an annular cutting blade. The cutting blade is brought into engagement with a peripherally located portion of the tissue specimen and rotated to produce a tangentially cut peripheral portion while a pulling force is applied to the tissue specimen through the central passageway. The pulling force rotates the tissue specimen within the bag to effect the production of the tangentially cut peripheral portion and to move the tangentially cut peripheral portion out of the patient's body. Gas pressure may be applied to inflate the bag to facilitate placement of the excising instrument.

20 Claims, 12 Drawing Sheets

(51) Int. Cl.
*A61B 17/32* (2006.01)
*A61B 17/34* (2006.01)
*A61B 90/00* (2016.01)

(52) U.S. Cl.
CPC . *A61B 17/3474* (2013.01); *A61B 2017/00287* (2013.01); *A61B 2017/320024* (2013.01); *A61B 2017/320064* (2013.01); *A61B 2090/0801* (2016.02)

(56) References Cited

U.S. PATENT DOCUMENTS

| | | | |
|---|---|---|---|
| 5,618,296 A | 4/1997 | Sorensen et al. | |
| 5,647,372 A | 7/1997 | Tovey et al. | |
| 6,039,748 A | 3/2000 | Savage et al. | |
| 6,045,566 A * | 4/2000 | Pagedas | A61B 17/32002 606/114 |
| 6,152,932 A | 11/2000 | Ternstrom | |
| 6,382,211 B1 | 5/2002 | Crook | |
| 6,409,733 B1 | 6/2002 | Conlon et al. | |
| 7,650,887 B2 | 1/2010 | Nguyen et al. | |
| 8,308,746 B2 * | 11/2012 | Pravong | A61B 17/32002 606/169 |
| 8,409,112 B2 | 4/2013 | Wynne et al. | |
| 8,486,087 B2 | 7/2013 | Fleming | |
| 8,652,147 B2 | 2/2014 | Hart | |
| 2006/0189920 A1 * | 8/2006 | Seeh | A61B 17/32002 604/22 |
| 2008/0039883 A1 * | 2/2008 | Nohilly | A61B 17/32002 606/180 |
| 2008/0221588 A1 | 9/2008 | Hollis et al. | |
| 2008/0255597 A1 | 10/2008 | Pravong et al. | |
| 2009/0043315 A1 | 2/2009 | Moon | |
| 2009/0192510 A1 | 7/2009 | Bahney | |
| 2013/0184536 A1 | 7/2013 | Shibley et al. | |
| 2013/0253267 A1 * | 9/2013 | Collins | A61B 17/221 600/104 |
| 2014/0148731 A1 | 5/2014 | Radl et al. | |
| 2015/0272620 A1 * | 10/2015 | Zisow | A61B 17/3205 600/204 |
| 2015/0320409 A1 | 11/2015 | Lehmann et al. | |

* cited by examiner

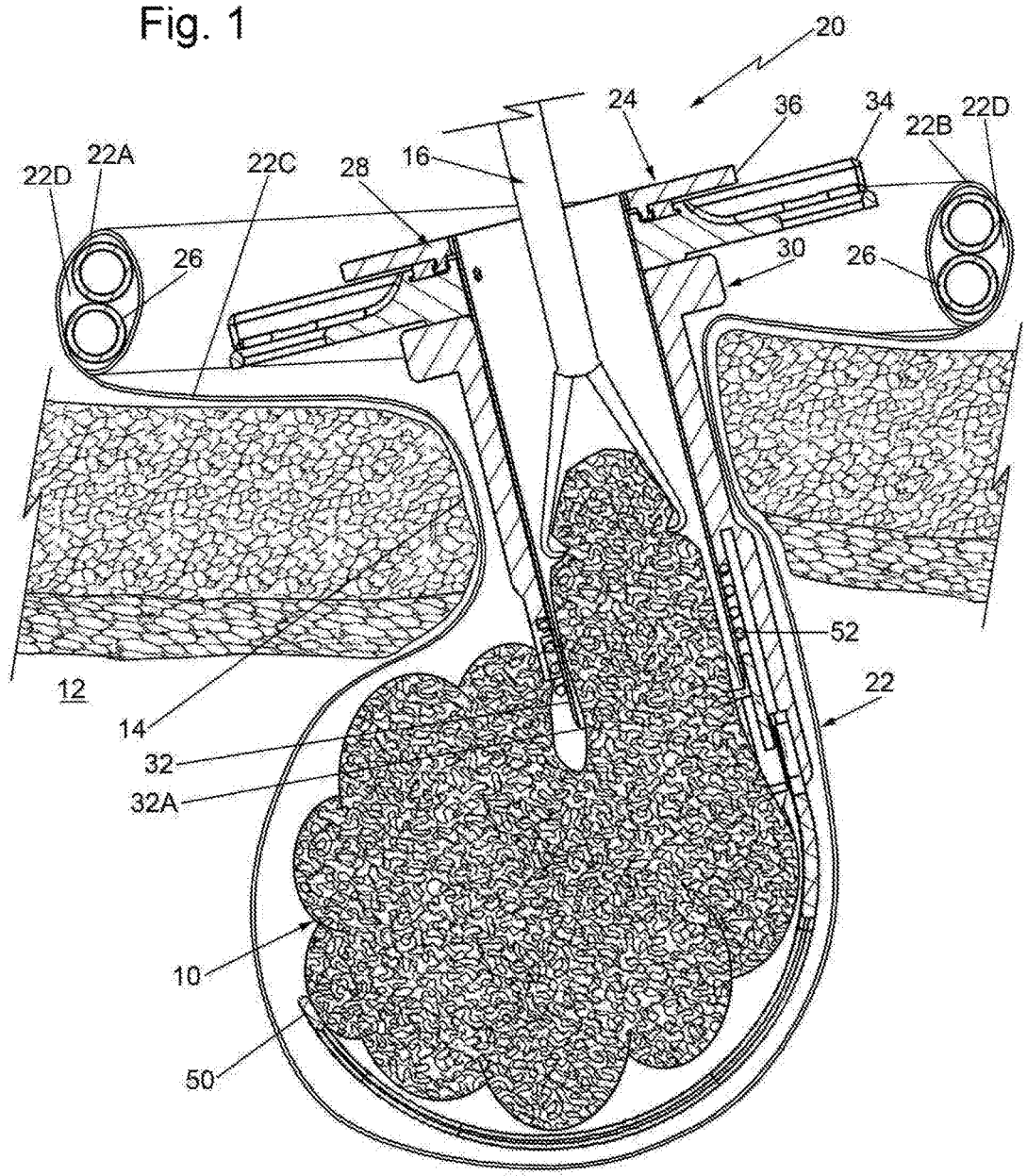

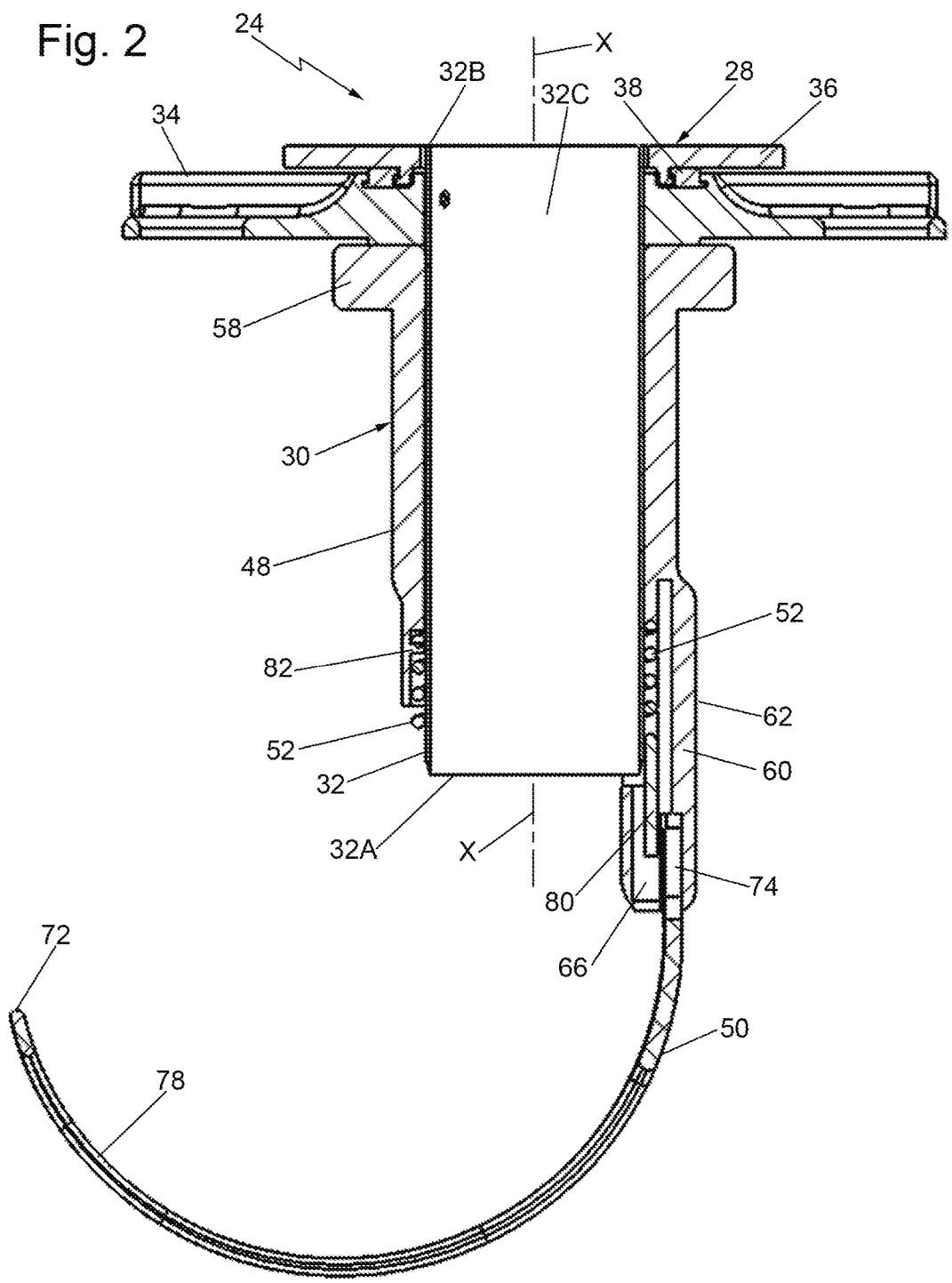

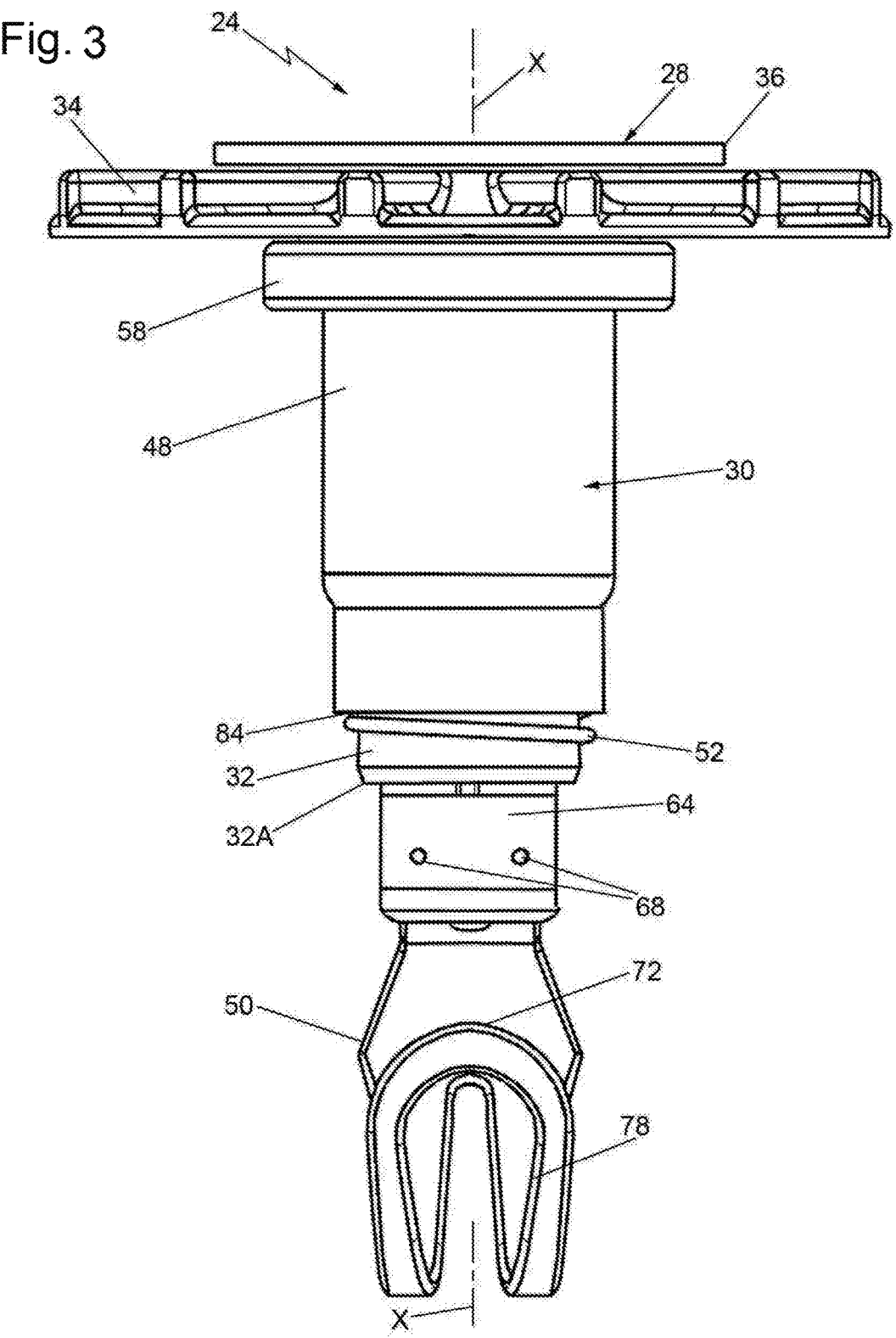

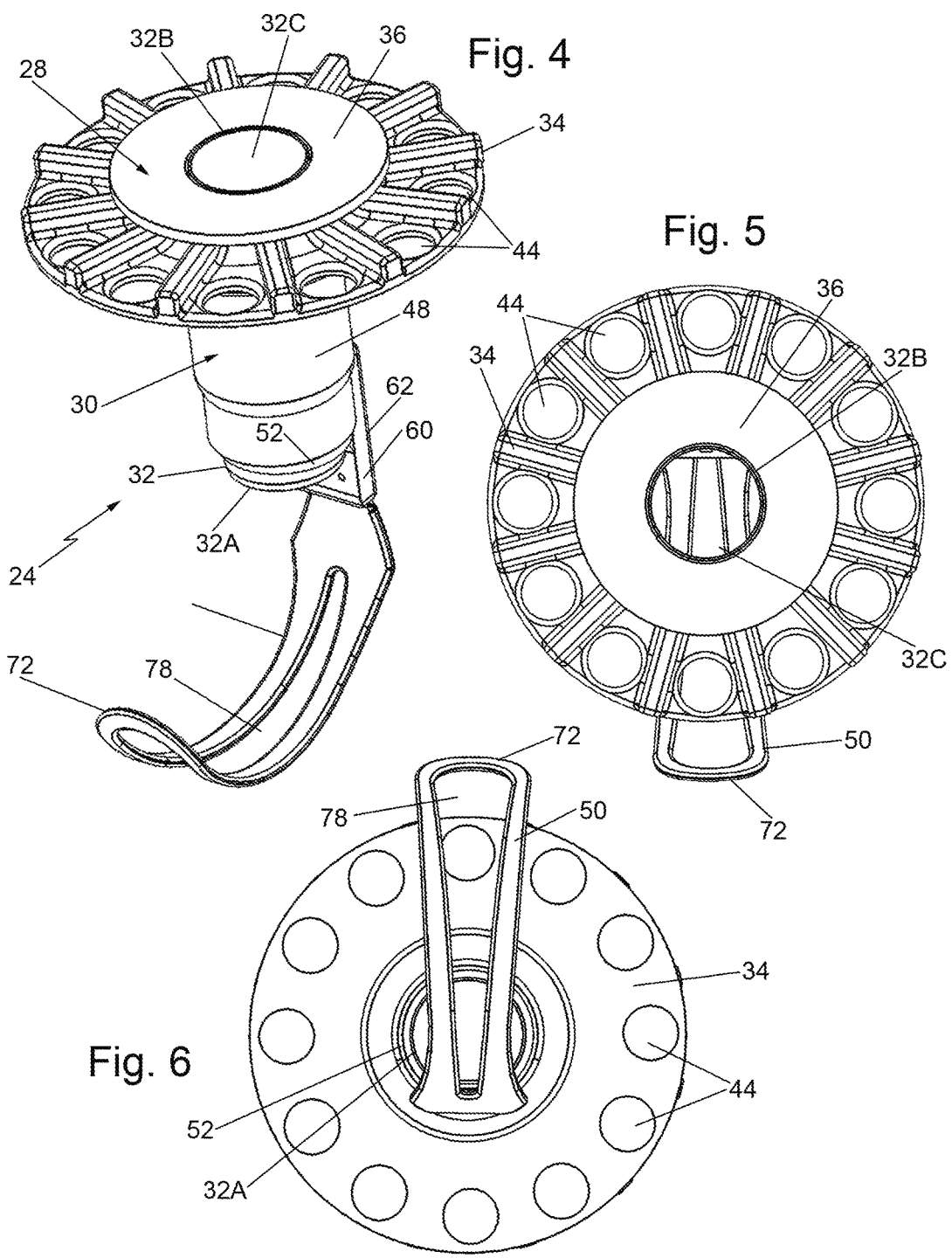

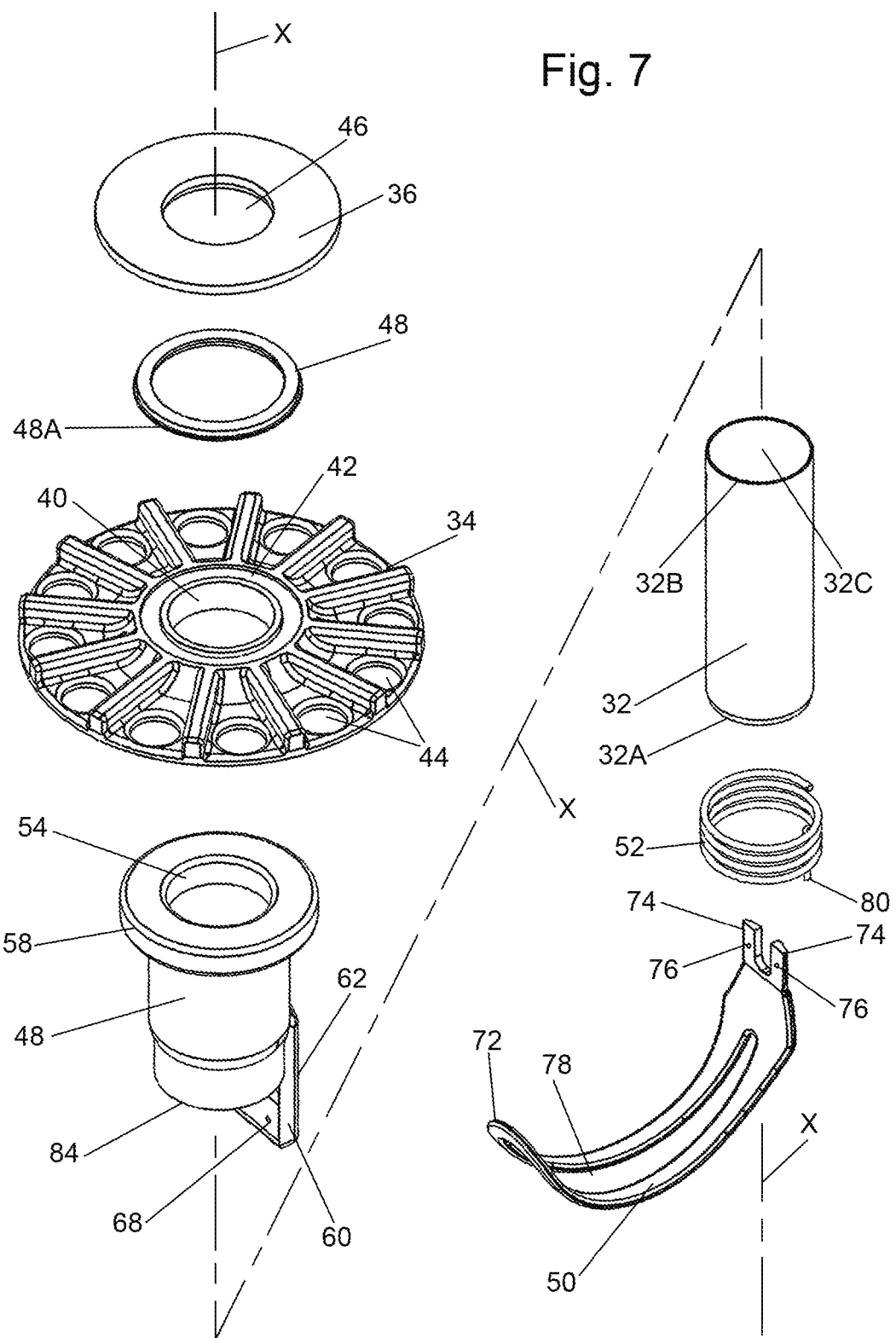

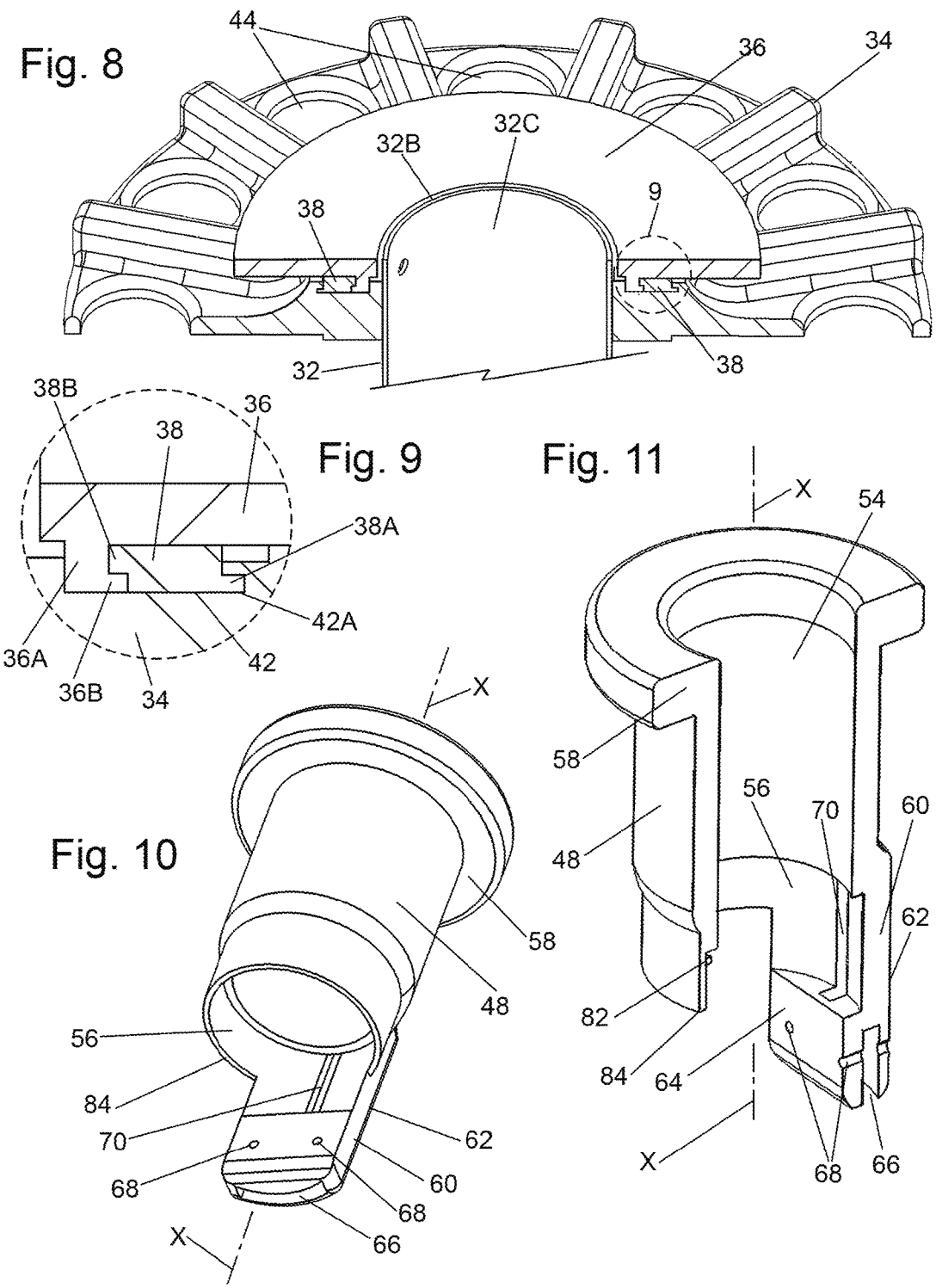

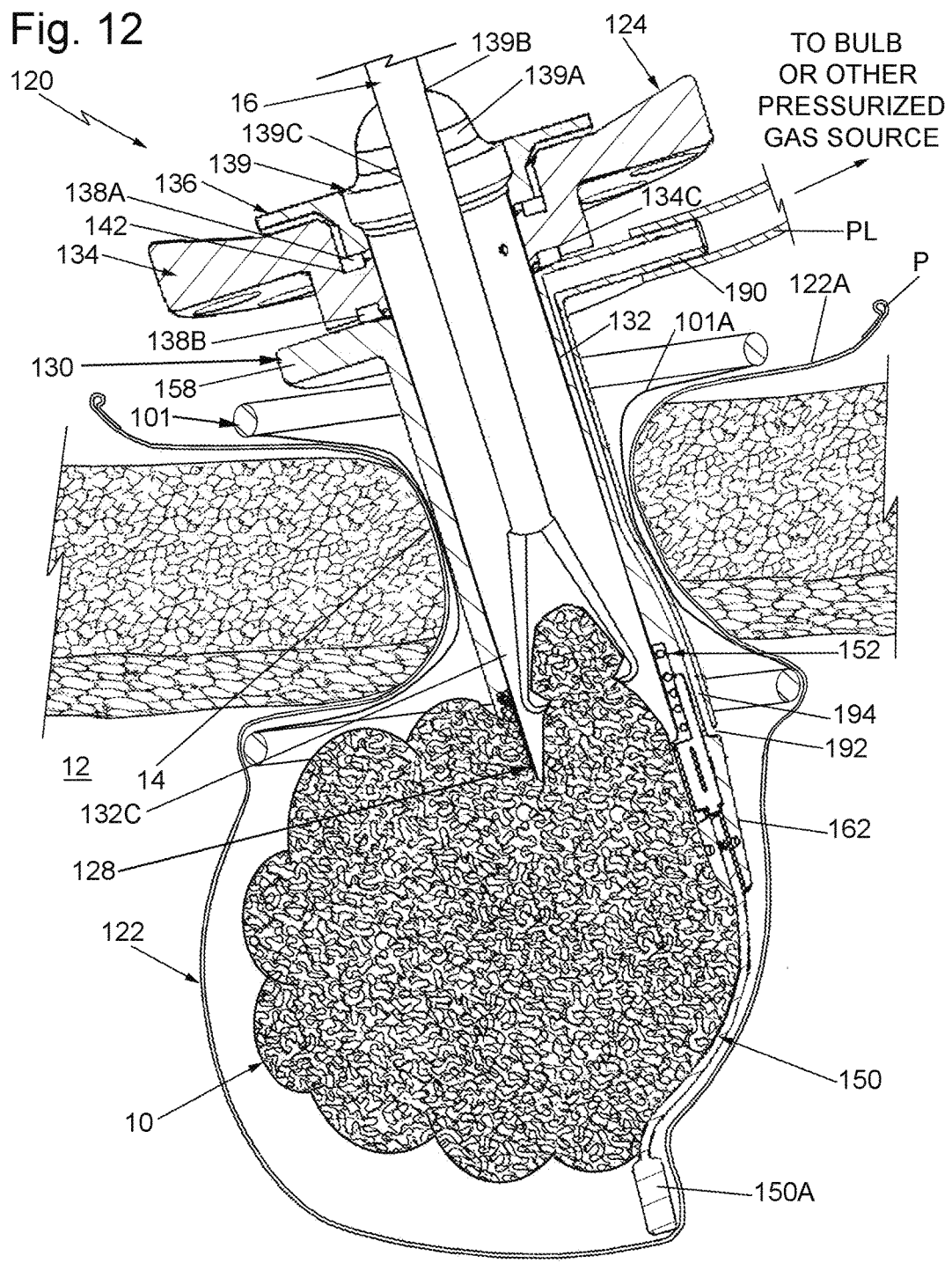

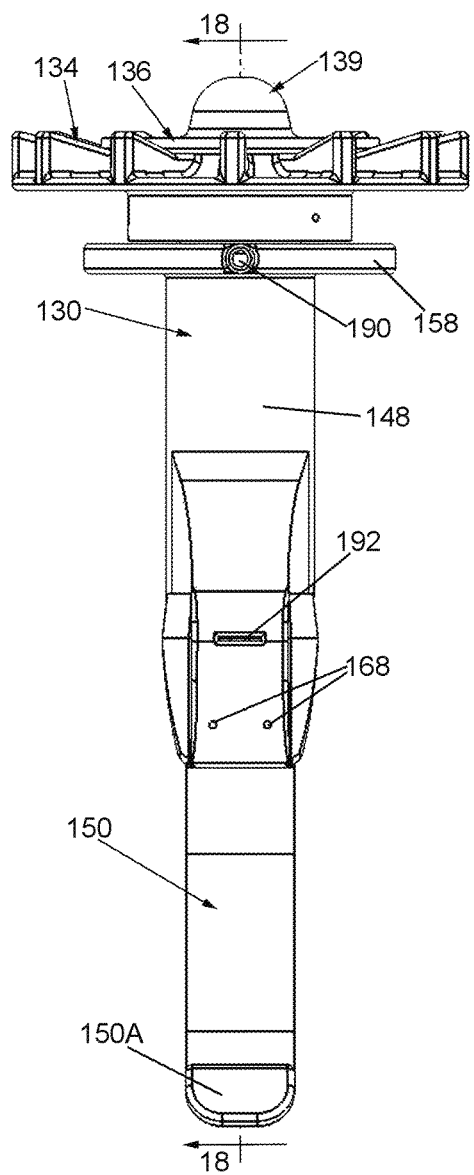
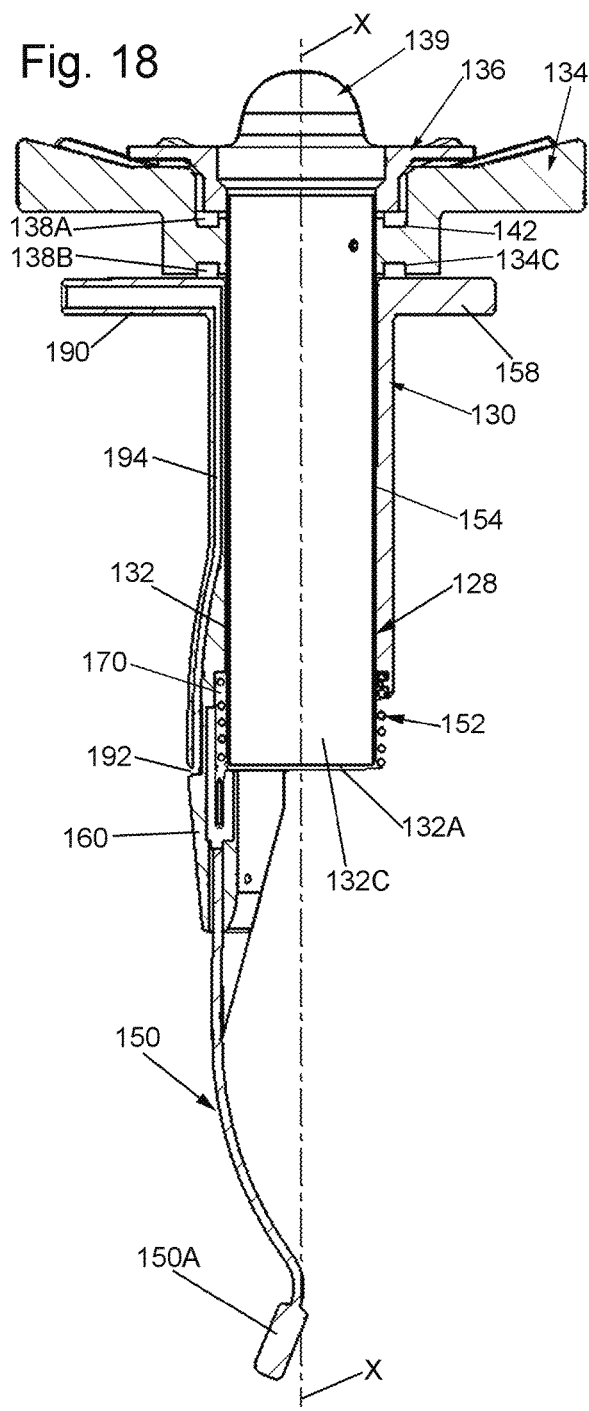
Fig. 17
Fig. 18

EXCISING INSTRUMENT, SYSTEM INCLUDING THE SAME, AND METHOD FOR REMOVING A TISSUE SPECIMEN OR ORGAN WITHIN A FLEXIBLE POUCH EXTENDING THROUGH A SMALL INCISION OR NATURAL OPENING IN A PATIENT

CROSS-REFERENCE TO RELATED APPLICATIONS

This utility application claims the benefit under 35 U.S.C. § 119(e) of Provisional Application Ser. No. 62/329,414 filed on Apr. 29, 2016 and Provisional Application Ser. No. 62/422,402 filed on Nov. 15, 2016, both entitled Excising Instrument, System Including The Same, And Method For Removing A Tissue Specimen Or Organ Within A Flexible Pouch Extending Through A Small Incision Or Natural Opening In A Patient. The entire disclosures of those provisional applications are incorporated by reference herein.

STATEMENT REGARDING FEDERALLY SPONSORED RESEARCH OR DEVELOPMENT

Not Applicable

SUBMITTED ON A COMPACT DISK

Not Applicable

FIELD OF THE INVENTION

The disclosed invention relates to medical devices and more particularly to systems and methods of use for removing an organ or tissue specimen that is located within a flexible pouch that extends through a small incision or natural opening in the body of a patient.

BACKGROUND OF THE INVENTION

More and more medical procedures for removing a targeted mass or specimen of tissue or an organ from the abdomen of a patient are accomplished laparoscopically to minimize scarring, infection, pain and other trauma. Typically the tissue specimen or organ is detached or freed from surrounding tissue using any conventional surgical techniques. Once that tissue specimen is free, it is ready for removal through the small incision into the abdomen (or via a suitable natural body orifice). If the targeted tissue specimen is too large to be removed as a whole unit through the incision or orifice, which quite commonly the case, the surgeon can resect it as necessary to reduce it in size or to a minimum of multiple pieces suitable for passing through the incision or orifice. Many of such procedures make use of a morcellator to reduce the size of the tissue specimen or organ.

As is known, morcellators are surgical instruments which typically take the form of a hollow cylinder that penetrates the abdominal wall and has a free distal end in the form of a high speed moving cutter or blade. Many morcellators include a central lumen or passageway through which a grasping instrument can be inserted to pull the tissue to be removed into a rotating cutter or blade to sever an extractable piece of that tissue, which is withdrawn out of the morcellator through its central passageway. While morcellators are effective for removing tissue from the body of the patient, the high-speed cutting action may free up some cells or other biological material, which can be dispersed within the peritoneal cavity. Thus, for example, if the tissue being removed is not known to be cancerous, but is in fact cancerous, there could be a release of cancer cells throughout the peritoneal cavity and from there elsewhere. Hence, it is possible for the process of morcellation to have an adverse effect on the patient.

In US2015/0320409, which is assigned to the same assignee as the subject invention, there is disclosed and claimed a system which addresses that problem by providing entrapment and collection systems and methods of entrapping and collecting biologic material produced during morcellation. Those systems include a collection bag which formed of a flexible sheet material having a hollow interior, a first mouth and a second mouth. The first mouth is openable to enable the biological structure to be disposed in the hollow interior and to enable a removal instrument, e.g., a morcellator, to be introduced therethrough to engage the biologic structure to effect a procedure on it. The second mouth enables a viewing instrument to be extended through it for visualizing the procedure and is closeable by a drawstring to entrap biologic material produced by the procedure after the removal instrument and viewing instrument have been removed, whereupon the collection bag may be withdrawn from the body of the patient.

Other systems have been disclosed in the patent literature to address the problem of containment of material produced during a morcellation procedure within the abdomen of a patent by means of a containment bag. For example, WO2015/164591 discloses a cut-resistant tissue guard removably insertable into a containment bag. The tissue specimen is isolated and contained within the containment bag and the guard is configured to protect the containment bag and surrounding tissue from incidental contact with sharp instrumentation used during morcellation and extraction of the tissue specimen. The guard is adjustable for easy insertion and removal and configured to securely anchor to the body opening. Protection-focused and containment-based systems for tissue removal are provided that enable minimally invasive procedures to be performed safely and efficiently. US2013/0184536 discloses a bag with one or more openings which is placed within a body cavity. Excised tissue is placed within the opening of a deflated bag. One or more opening in the bag are withdrawn outside the body cavity and the bag is inflated. Instruments, including laparoscopic visualization are placed within the inflated bag that remains within the body cavity. The tissue retained within the body cavity is morcellated/crushed/reduced and removed. The bag is deflated and removed with the residual tissue/blood/fluids inside. The tissue to be removed is retained in the bag which prevents potentially harmful material such as cancerous cells from being released in the body cavity.

The patent literature also includes various other relatively small, rolled-up or folded bags or pouches that are deployed and opened in the abdominal cavity where tissue is placed in them and then they are closed for retraction. See, for example, U.S. Pat. Nos. 8,652,147, 8,486,087, 8,409,112, 7,650,887, 6,409,733, 5,647,372, 2009/0043315, 2009/0192510 and 2008/0221588.

In our co-pending U.S. patent application Ser. No. 14/986,890, filed on Jan. 4, 2016, entitled Systems For Removing A Tissue Specimen Or Organ Through A Small Incision Or Natural Opening In A Patient, which is assigned to the same assignee as the subject invention, and whose entire disclosure is incorporated by reference herein, there is disclosed and claimed a system and method for effecting the removal of a tissue specimen or organ through a small incision in the body of a patient making use of a collection bag and associated cutter components. That system is simple in construction and easy to use, which eliminates the need for power morcellators while minimizing the chances of dispersion of unwanted portions of the tissue specimen or organ, cells or other biological material into the peritoneum or other internal portion of the body in which the tissue specimen or organ is located. In particular, the system of that published application includes a device for cutting the tissue specimen or organ. The device comprises a passer and a wire. The passer comprises a long flexible member having a distal end and a proximal end. The passer has an opening located adjacent the distal end and extending backward toward the proximal end. The wire serves as the cutter for the system and has a distal end and a proximal end. The distal end of the wire is connected to the passer adjacent the proximal end of the passer. The distal end of the passer is configured to be introduced through the mouth portion of the bag or pouch to pass between the interior surface of the bag or pouch and the tissue specimen or organ in a path around the tissue specimen or organ and back out through the mouth portion of the bag or pouch to carry the wire around the tissue specimen or organ through that path so that the distal end of the wire is located outside the body of the patient and a proximal portion of the wire is also located outside the body of the patient. The distal end portion of the wire and the proximal portion of the wire are configured to be pulled so that the wire cuts though the tissue specimen or organ within the bag or pouch to form plural pieces. The plural pieces of the tissue specimen or organ can then be removed through the mouth portion of the bag or pouch while the bag or pouch is within the body of the patient.

While the device of our aforementioned published patent application is suitable for its intended purposes, it nevertheless leaves something to be desired from the standpoint of ease of use of the cutter. Thus, a need exists for a system and methods of use which overcome the drawbacks of the prior art. The subject invention addresses that need.

SUMMARY OF THE INVENTION

In accordance with one aspect of this invention an excising instrument is provided for use in a system for removing an organ or tissue specimen from the body of a patient through an opening in the patient's body. The organ or tissue specimen is located within a flexible bag or pouch located within an interior space in the body of the patient, with a mouth portion of the bag or pouch being located outside of the body of the patient. The instrument comprises a guide member, and a cutter. The guide member has a distal end portion configured for introduction through the mouth portion of the bag or pouch to a position adjacent the organ or tissue specimen, a proximal end portion configured for location outside the body of the patient, and a longitudinal axis extending between the distal end portion and the proximal end portion. The cutter is mounted for rotation within the guide member about the longitudinal axis. The cutter comprises a tubular member having a central passageway and a distal end in the form of an annular cutting blade. The annular cutting blade is configured to be brought into engagement with a peripherally located portion of the tissue specimen or organ to cut into that peripherally located portion as the cutter is rotated about the longitudinal axis to produce a tangentially cut peripheral portion, whereupon the tangentially cut peripheral portion will be in communication with the central passageway. The central passageway is configured for receipt of a pulling device extended therethrough to pull the tangentially cut peripheral portion into and through the central passageway in the proximal direction, whereupon the tangentially cut peripheral portion is withdrawn out of the body of the patient.

In accordance with one preferred aspect of this invention the guide member additionally comprises a blade blocking member interposed between the annular cutting blade and the bag or pouch.

In accordance with another preferred aspect of this invention the guide member additionally comprises a passer, e.g., an elongated arcuate tongue member, configured for location interposed between the bag or pouch and the tissue specimen or organ. The tongue member is configured to curve around a peripheral portion of the tissue specimen or organ to facilitate the orientation of the tissue specimen or organ within the bag or pouch for proper cutting.

In accordance with another preferred aspect of this invention the instrument additionally comprises a retractable sleeve configured to be automatically extended from a retracted position to an extended position. When the sleeve is in the extended position it covers the annular cutting blade so that the annular cutting blade does not engage the bag or pouch if the annular cutting blade is not surrounded by portions of the tissue specimen or organ.

In accordance with another preferred aspect of this invention the cutter additionally comprising a handle. The handle is located outside of the body of the patient at the proximally located portion of the guide member. The handle is configured to be rotated about the longitudinal axis to effect the rotation of the annular cutting blade about the longitudinal axis.

In accordance with another preferred aspect of this invention the instrument additionally comprises a counter pressure member configured to have a counter-force applied thereto as the pulling device pulls the tangentially cut peripheral portion into and through said central passageway in the proximal direction.

In accordance with another preferred aspect of this invention the guide member comprises a gas passageway, configured for coupling to a source of inflation gas, for enabling the bag or pouch to be inflated so that the tissue specimen or organ can be readily moved or positioned within the bag or pouch.

In accordance with another preferred aspect of this invention the gas passageway extends through a portion of the guide member between an inlet port and an outlet port, with the outlet port being located within the bag or pouch when the guide member is inserted therein, with the inlet port being configured to be coupled to the source of inflation gas located outside the body of the patient.

In accordance with another preferred aspect of this invention the source of inflation gas comprises a compressible bulb.

In accordance with another preferred aspect of this invention the instrument additionally comprises a sealing member configured to engage a portion of the pulling device to prevent egress of the gas through an interface between the sealing member and the portion of the pulling device, while enabling the pulling device to pull the tangentially cut peripheral portion of the tissue specimen or organ out of the body of the patient.

In accordance with another preferred aspect of this invention the sealing member comprises a pliable dome having an opening to allow passage of the pulling device therethrough while maintaining a pressurized environment with the body of the patient.

Another aspect of this invention is a system for removing an organ or tissue specimen from the body of a patient through an opening in the patient's body. The system comprises a flexible bag or pouch and an excising instrument. The flexible bag or pouch has a hollow interior portion in which the specimen or organ is located and a mouth portion in communication with the hollow interior portion. The hollow interior portion is configured for location within an interior space in the body of the patient and with a mouth portion of the bag or pouch being located outside of the body of the patient. The instrument comprises a guide member, and a cutter. The guide member has a distal end portion configured for introduction through the mouth portion of the bag or pouch to a position adjacent the organ or tissue specimen, a proximal end portion configured for location outside the body of the patient, and a longitudinal axis extending between the distal end portion and the proximal end portion. The cutter is mounted for rotation within the guide member about the longitudinal axis. The cutter comprises a tubular member having a central passageway and a distal end in the form of an annular cutting blade. The annular cutting blade is configured to be brought into engagement with a peripherally located portion of the tissue specimen or organ to cut into that peripherally located portion as the cutter is rotated about the longitudinal axis to produce a tangentially cut peripheral portion, whereupon the tangentially cut peripheral portion will be in communication with the central passageway. The central passageway is configured for receipt of a pulling device extended therethrough to pull the tangentially cut peripheral portion into and through the central passageway in the proximal direction, whereupon the tissue specimen or organ is rotated within the bag or pouch and the tangentially cut peripheral portion is withdrawn out of the body of the patient.

In accordance with another preferred aspect of the system of this invention the system additionally comprises a retractor configured for insertion into the mouth portion of the bag or pouch for enabling the excising instrument to be introduced therethrough.

In accordance with another preferred aspect of the system of this invention the retractor includes a sidewall configured for engaging a portion of the periphery of the excising instrument to form a fluid-tight seal therebetween.

In accordance with another preferred aspect of the system of this invention the flexible bag or pouch includes a ring located adjacent the mouth of the bag or pouch and about which portions of the bag or pouch can be rolled up.

Another aspect of this invention is a method for cutting a tissue specimen or organ located within the body of a patient to enable its removal from the body of the patient. The method comprises providing a flexible bag or pouch having a hollow interior and a mouth portion in communication with the hollow interior. The flexible pouch is disposed within the body of a patient, with a tissue specimen or organ located within the hollow interior of the bag or pouch, and with the mouth portion of the bag or pouch extending through an opening in the body of the patient. The method additionally entails providing an instrument comprising a guide member having a longitudinal axis and a cutter mounted for rotation within the guide member about the longitudinal axis. The cutter comprises a tubular member having a central passageway and a distal end in the form of an annular cutting blade. The annular cutting blade is brought into engagement with a peripherally located portion of the tissue specimen or organ while rotating the cutter about the longitudinal axis to cut into the peripherally located portion to produce a tangentially cut peripheral portion, whereupon the tangentially cut peripheral portion will be in communication with the central passageway. A pulling device is extended through the central passageway to pull the tangentially cut peripheral portion into and through the central passageway in the proximal direction, whereupon the tissue specimen or organ is rotated within the bag or pouch and the tangentially cut peripheral portion is withdrawn out of the body of the patient.

In accordance with one preferred aspect of the method of this invention the bag or pouch is inflated by a gas so that the tissue specimen or organ can be readily moved or positioned within the bag or pouch.

In accordance with another preferred aspect of the method of this invention a sealing member is provided and configured to engage a portion of the pulling device to prevent the egress of the gas through an interface between the sealing member and the portion of the pulling device while enabling the pulling device to pull the tangentially cut peripheral portion out of the body of the patient.

In accordance with another preferred aspect of the method of this invention a retractor is inserted into the mouth portion of the bag or pouch to provide an access port for inserting of the excising instrument therethrough.

BRIEF DESCRIPTION OF THE DRAWING FIGURES

FIG. 1 is an illustration of the system of this invention showing an excised tissue specimen or organ disposed within a flexible bag or pouch located within the insufflated abdomen of a patient, and with an excising instrument of the system extending into the bag or pouch in the process of cutting away and removing the tissue specimen or organ;

FIG. 2 is an enlarged side elevation view in vertical section of the excising instrument shown in FIG. 1;

FIG. 3 is front elevation view of the excising instrument shown in FIG. 2;

FIG. 4 is a somewhat reduced isometric view of the excising instrument shown in FIGS. 1-3;

FIG. 5 is a top plan view of the excising instrument shown in FIG. 4;

FIG. 6 is a bottom plan view of the excising instrument shown in FIG. 4;

FIG. 7 is an exploded isometric view of the various components making up the excising instrument shown in FIG. 4;

FIG. 8 is an enlarged isometric view, in vertical section, of a portion of the excising instrument shown in FIG. 4;

FIG. 9 is an enlarged sectional view of the portion of the excising instrument shown within the broken circle designated by the number 9 in FIG. 8;

FIG. 10 is an isometric view of one of the components, i.e., the guide member, shown in FIG. 7;

FIG. 11 is a somewhat enlarged isometric view, partially in vertical section of the guide member shown in FIG. 10;

FIG. 12 is an illustration of a more preferred exemplary system of this invention showing an excised tissue specimen or organ disposed within a flexible bag or pouch located within the insufflated abdomen of a patient, and with an excising instrument of the system extending into the bag or pouch in the process of cutting away and removing the tissue specimen or organ;

FIG. 15A is an enlarged isometric view of one component of the instrument shown in FIGS. 14 and 15;

FIG. 17 is slightly reduced rear elevation view of the rear side of the excising instrument of FIG. 12; and FIG. 18 is a slightly enlarged cross-sectional view of the excising instrument of FIG. 12 taken along line 18-18 of FIG. 17.

DETAILED DESCRIPTION OF THE PREFERRED EMBODIMENTS

Figure 13:
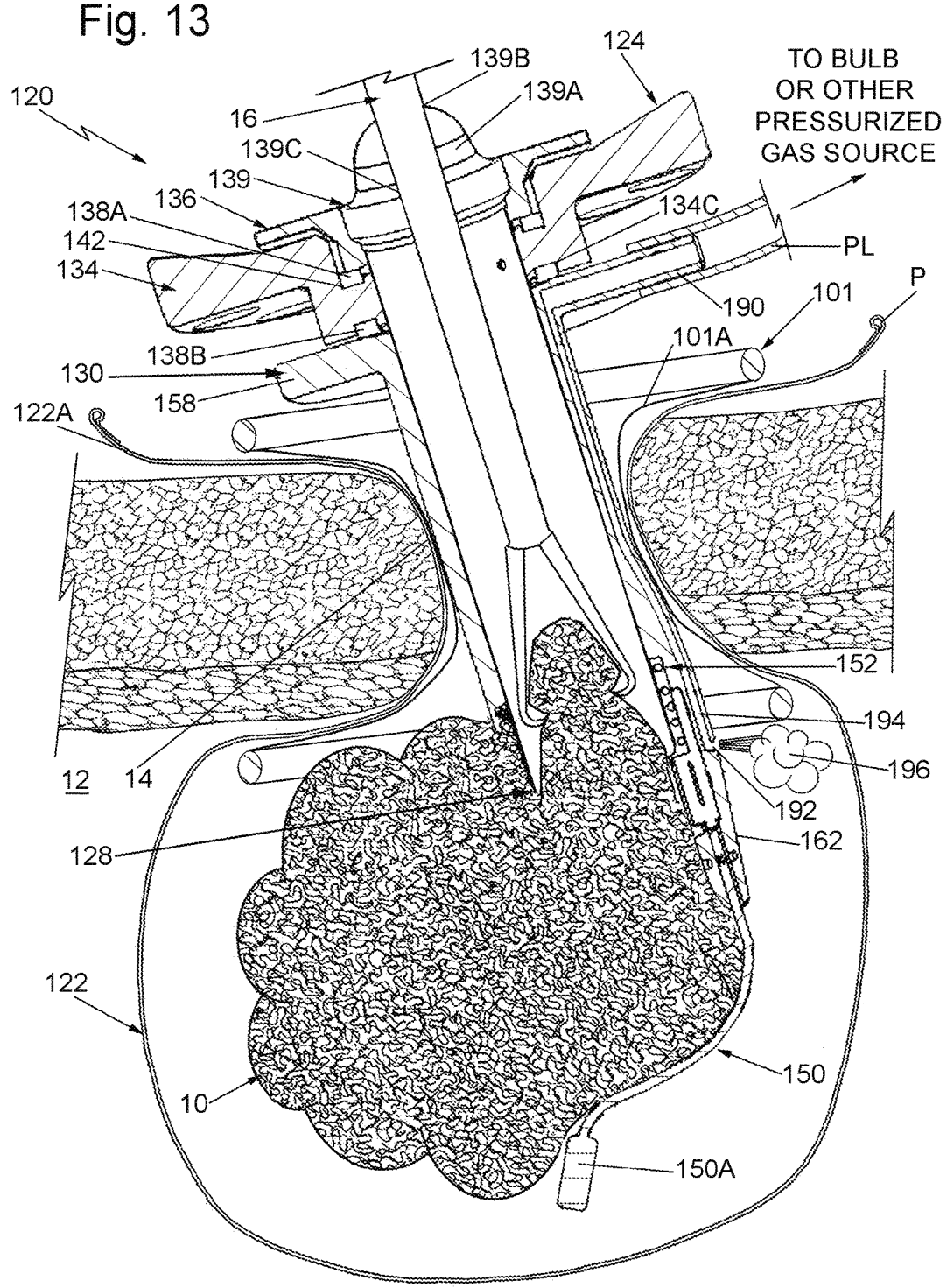
FIG. 13 is an illustration, similar to FIG. 12, but showing the bag or pouch being inflated to facilitate the instrument's placement and tissue cutting operation.

Referring now to the drawings wherein like characters refer to like parts there is shown in FIG. 1 one exemplary embodiment of a tissue specimen or organ removing system 20. The system 20 basically comprises a receptacle, e.g., a bag or pouch 22, or any other hollow flexible container, and an excising instrument 24. The system 20 is configured for facilitating the removal of a large organ or tissue specimen 10 from within a space, e.g., the peritoneal cavity 12, in the body of a patient, via an opening or incision 14 to that space. The opening may be an incision 14, like shown in FIG. 1, or natural body opening, such as the vagina. In accordance with one aspect of this invention the incision/opening can be smaller than the organ/tissue specimen 10 to be removed.

The bag or pouch 22 is constructed in accordance with the teaching of our above identified patent application Ser. No. 14/986,890, now U.S. Pat. No. 9,986,986, and basically comprises a hollow member formed of any suitable flexible material, e.g., polyurethane film. The bag includes a pair of flaps 22A and 22B contiguous with the mouth 22C of the bag. Each flap includes a first channel (not shown) to accommodate a support ring (not shown), and a second channel 22D to accommodate a split ring 26. The support ring is formed of a resilient material and is extended through the first passageway in each flap, whereupon the bag or pouch can be collapsed and rolled up, so that it can be inserted through a trocar (not shown) that extends through the incision 14 to a position within the peritoneal space 12, adjacent the tissue specimen or organ 10 to be removed. A grasper instrument of any suitable type (not shown) can be used to grasp the bag to ensure that its mouth 22C is open and to pull the open mouth to a desired position with respect to the tissue specimen or organ, which had previously been excised or freed from adjacent tissue. A second grasper instrument (not shown) can be used to move the excised tissue specimen or organ into and through the mouth of the bag, while holding the bag in place with the first grasper instrument. The flaps contiguous with mouth of the bag can then be pulled so that the mouth of the bag is located outside of the patient's body, whereupon the resilient nature of the support ring causes the mouth of the bag to spring open. At that point the bag is ready to have the split ring 20 inserted into the second channels in its flaps. To that end, one end of a first split ring section is inserted into one end of the second channel in one flap and slid down that channel until the end of the first split ring section exits an opposite end of that channel. A second split ring section is inserted into one end of the second channel in the other flap and extended therethrough until it exits the opposite end of that channel. The two ends of the first and second split ring sections are then connected together to form a continuous ring (referred to as the "split ring"). Portions of the bag contiguous with its mouth can then be rolled up about the split ring to cause those portions to wrap around the split ring and the support ring, thereby pulling the tissue specimen or organ closer to the incision or opening 14. Once that has been accomplished the excising instrument 24 can be inserted within the bag and operated.

The excising instrument 24 will be described in detail shortly. Suffice it for now to state that it is constructed to be operated in such a manner that a rotatable cutting blade of the instrument engages peripheral portions of the tissue specimen or organ, while some pulling device, e.g., a grasper, pulls on that tissue specimen or organ. That pulling action rotates the tissue specimen or organ within the bag, whereupon the engagement of the rotating cutting blade with the rotating tissue specimen or organ tangentially cuts away portions of the tissue specimen or organ, somewhat like the peeling of the skin of an apple. Continued pulling on the tangentially cut portions of the tissue specimen or organ by the pulling device removes those portions from the body of the patient, while the bag traps any debris, cells, etc., produced during the cutting action within the bag. After the entire tissue specimen or organ has been excised and removed from within the bag, the instrument can be withdrawn from the bag, and the bag can then be removed from the patient's body through the incision 14.

Turning now to FIGS. 2-7 the details of the excising instrument 24 will now be described. It basically comprises a cutter 28 and a guide 30. The cutter 28 is rotatably mounted within the guide 30 and comprises an assembly four components, namely, a tubular cutting member 32, a handle or dial 34, a counter pressure member 36 and a washer 38. The tubular cutting member 32 is an elongated tube having a distal end 32A, a proximal end 32B, and passageway 32C extending between those ends. A central longitudinal axis X extends down the center of the passageway 32C and serves as the axis about which the cutter is rotated. The tubular cutting member 32 is of circular profile, with the distal end 34A being in the form of a sharp annularly shaped cutting edge or blade. The tubular cutting member 34 can be formed of any suitable material, e.g., hardened stainless steel. The handle 34 of the cutter 28 is in the form of an annular disk-like member or dial that can be formed of any suitable material, e.g., a plastic such as ABS or polycarbonate. The dial includes a central hole 40 through which the proximal end 32A of the tubular cutting member 32 extends and to which it is fixedly secured. The top surface of the handle or dial 34 includes an annular recess 42 (FIGS. 2, and 7-9) which is concentric with the center hole 40. As best seen in FIG. 9, the recess 42 is undercut at 42A. The annular recess 42 is configured to receive the washer 38. The handle or dial 32 also includes a plurality of apertures or openings 44 that are equidistantly spaced from one another and located adjacent the outer periphery of the handle or dial. Each of the openings 44 is configured to receive a finger of a user to effect the rotation of the cutter 28 with respect to the guide 30, as will be described later.

The counter-pressure applying member 36 can be formed of any suitable material, e.g., a plastic such as ABS or polycarbonate, and basically comprises a disk-like body of circular profile having a central opening 46 (FIG. 7). The central opening 46 is configured to receive the proximal end 32B of the tubular cutting member 32. As best seen in FIG. 9, the undersurface of the counter-pressure applying member 36 includes an annular downwardly projecting wall 36A immediately adjacent the central opening 46. The lower end of the annular wall 36A is in the form of an annular flange 36B which projects radially outward, thereby leaving an annular space between the undersurface of the counter-pressure applying member 38 and the adjacent surface of the flange 36B. This annular space is configured to receive an annular edge portion of the washer 38 to be described hereinafter.

The washer 38 is best seen in FIGS. 7 and 9 and is preferably formed of any suitable low friction material, such as Teflon®. As mentioned above the washer is configured to be received within the annular recess 42 in the handle or dial 34, such that it is interposed or sandwiched between the undersurface of the counter-pressure applying member 36 and the bottom surface of the annular recess 42. This feature enables one to readily rotate the handle or dial to thereby rotate the tubular cutting member 32, with respect to the counter-pressure applying member, while one applies downward pressure on the counter-pressure applying member during use of the instrument, as will be described later. The washer is a ring-like member, whose inner peripheral surface is in the form of an inwardly projecting annular edge 38A (FIG. 9) and whose outer peripheral surface is in the form of an outwardly projecting annular edge 38B. The edge 38B is contiguous with the top surface of the washer, while the edge 38A is contiguous with the bottom surface of the washer. The annular edge 38A is configured to be received within the undercut portion 42A of the recess 42, thereby holding the washer in that recess. The annular edge 38B of the washer is received within the space between the undersurface of the counter-pressure applying member 36 and the flange 36B of that member, thereby rotationally securing the counter-pressure applying member to the handle or dial 34.

Turning now to FIGS. 2, 3 and 7, the details of the guide 28 will now be described. Thus, as can be seen the guide 28 basically comprises an assembly of a guide body 48, a passer 50, and a retractable sleeve 52. The guide body 48 can be formed of any suitable material, e.g., a plastic such as ABS or polycarbonate, and is a generally tubular member having a central passageway 54 extending through it. The passageway 54 is centered about a central longitudinal axis X and is of an internal diameter just slightly larger than the external diameter of the tubular cutter member 32 to receive the tubular cutter member therein. The lower or distal portion of the passageway 54 is in the form of an annular recess 56. The proximal end of the guide body 48 is in the form of an outwardly extending shoulder or flange 58. The lower section of the guide body 48 terminates in a thickened wall 60 that projects downward. The projecting wall 60 has an arcuate outer surface 62 and a planar inner surface 64. The wall includes an internal cavity 66 extending upward from the free end of the wall. The internal cavity is configured to receive portions of the passer 50 to fixedly mount the passer thereon. To that end, two apertures 68 extend through the wall 60 and are in communication with the cavity 66. The apertures are configured to receive respective pins (not shown) extending through respective tines (to be described shortly) making up a portion of the passer 50. The inner surface of the annular recess 56 at the location of the projecting wall 60 includes an elongated linear channel 70 extending parallel to the longitudinal central axis X. The channel is configured to receive a portion of the retractable sleeve 52.

The passer 50 is best seen in FIGS. 2-4 and 7, and basically comprises an arcuate elongated tongue shaped member. The tongue-shaped member is semi flexible and can be formed of any suitable material, e.g., high density polyethylene. The distal or free end 72 of the passer is flared and rounded. The opposite end of the passer comprises a pair of tines 74 extending parallel to each other. The tines are configured to be received within the cavity 66 to fixedly secure the passer to the guide body. To that end, each tine includes an aperture 78 which is configured to be axially aligned with a respective aperture 68 in the projecting wall. The aligned apertures are configured to accommodate respective pins (not shown) to fixedly secure the passer to the guide body 48. A slot 78 extends from a point adjacent the free end 72 of the passer to a point adjacent the tines 74.

The passer is of the arcuate shape so that when the instrument 20 is in place within the bag or pouch it is located between the inner surface of the bag or pouch 22 and the outer surface of the excised tissue specimen or organ 10. That action effectively cradles and supports the tissue specimen or organ during the operation of the instrument. Moreover, the arcuate nature of the passer ensures that when the instrument is inserted into the bag or pouch the cutter will be oriented in a desired somewhat angular orientation to engage a peripheral portion of the tissue specimen or organ, like shown in FIG. 1. In particular, the passer serves the purpose of aligning the cutter at the perimeter of the tissue specimen or organ in a generally tangential orientation relative to the specimen or organ. This is important as ideally one wants the tissue specimen or organ to rotate to the extent possible (so that it is cut much like peeling an apple in a continuous strip). If the cutter is not oriented properly it could core into the middle of the tissue specimen or organ, thereby jamming the instrument with tissue.

The retractable sleeve 52 is provided to protect the bag or pouch from being cut by the cutter. In the exemplary embodiment the retractable sleeve 52 comprises a helical compression spring. The spring 52 is located within the annular recess 56. The inner diameter of the helical spring is just slightly greater than the outer diameter of the tubular cutter member 32 of the cutter to accommodate the distal end portion of the tubular cutter member 32 within it. One end of the spring 52 is the form of a linear extension 80 that extends parallel to the axis X and which is located in the linear channel 70 of the recess 56. As best seen in FIG. 11 a ring-like projection 82 projects inward from the inner surface of the recess 56. As best seen in FIG. 2, the projection 82 is configured to be located between immediately adjacent coils of the spring 52 to hold the spring within the recess 56. The spring is normally biased such that at least one coil at the lower or free end of the spring extends beyond the blade 32A of the cutter, thereby covering the blade. This feature is of considerable importance in the interest of safety. In particular, the retractable sleeve serves to cover the blade's edge so that the material making up the bag or pouch 22, e.g., flexible film, does not come into contact with the blade edge in scenarios where the blade might not be surrounded by tissue and the differential pressure in the peritoneal space 12 might be inclined to push the film of the bag or pouch into the blade edge. The sleeve 52 is normally in its extended position such that the blade edge 32A is not exposed.

Use of the instrument 24 is as follows: After the bag or pouch 22 has been introduced into the body of the patient and the tissue specimen or organ 10 located within the bag or pouch and the mouth portion of the bag or pouch has been rolled up about the split ring 26 as described above, the guide 30 is ready for insertion into the bag or pouch. To that end, the rounded free end 72 of the passer 50 of the guide is introduced into the mouth of the bag or pouch so that it passes between the inner surface of the bag or pouch and the excised tissue specimen or organ 10. The guide is advanced until the guide body 48 is fully inserted into the mouth of the bag or pouch. The shoulder portion 58 of the guide prevents the guide from being inserted too far into the patient. The cutter 28 is then inserted into the guide 30, i.e., the tubular cutter member 32 extended through the passageway 54 in the guide and through the retractable sleeve 52, until the blade 32A contacts the tissue specimen or organ, with the cutter 28 being aligned at the perimeter of the tissue specimen or organ 10 in a generally tangential orientation. Then any type of tissue grasper instrument or device 16 is inserted through the passageway 32C of the tubular member 32 so that it can grasp and the tissue specimen or organ, whereupon the tissue specimen or organ can be pulled in a proximal direction toward the blade 32A like shown in FIG. 1. The cutter 28 is then rotated or spun using its handle or dial 34, while pulling on the tissue specimen or organ with the grasper 16. As the tissue specimen or organ is pulled by the grasper, it tends to want to force the cutter out of the bag or pouch. In order to counter this force, a force is applied by hand to the counter-pressure member. In particular, at the same time that the handle or dial is rotated, a force is applied to the counter-pressure member 36 so that the action of pulling on the tissue specimen or organ with the grasper 16 does not force the guide and cutter out of the mouth of the bag or pouch. Typically, one person pulls on the tissue specimen or organ with the grasper while pushing on the counter-pressure member 36, thereby holding it stationary, and a second person turns the dial 34 of the cutter with respect to the stationary counter-pressure member. Inasmuch as the washer 38, which is interposed between the dial 34 and the counter-pressure member 36, is formed of a low friction material, the dial can be rotated easily with respect to the counter-pressure member.

The downwardly projecting wall 60 serves as a blade-edge-blocking member adjoining the passer 50 and blocks about 15% of the blade. This helps to keep the blade in a tangential orientation relative to the tissue specimen or organ 10. It also prevents tissue that is cut from the tissue specimen or organ from completely filing the passageway 32C of the cutter, which could result in "packing" of the cutter making it harder to rotate and extract tissue.

As mentioned earlier, the retractable sleeve, e.g., spring 52, covers the blade edge 32A so that the film of the bag or pouch does not come into contact with the blade edge in scenarios where the blade might not be surrounded by tissue and the differential pressure in the peritoneal space might be inclined to push the film of the bag into the blade edge. The sleeve is normally in its extended position such that the blade edge is not exposed. When tissue is grasped and pulled towards the blade it causes the sleeve retract and the blade edge becomes exposed allowing it to cut into the tissue. If there is no tissue present, the sleeve will return to its extended position. One advantage of using a spring as a sleeve is that it pivots as well as moving linearly. This can be useful if tissue pulled into the passageway of the cutter from one side only. In this case the spring would retract on the tissue side only and still remain extended on the opposite side.

In accordance with one preferred embodiment to the invention the film making up the bag or pouch or pouch is 0.006 inches thick and has a durometer of approximately 90 shore A and a 100% modulus of 1,700 psi. The combination of the film thickness and material properties make the film stiff enough such that the peritoneal insufflation pressure does not cause the film to conform around the spring/shield and into contact with the blade edge.

Turning now to FIGS. 12-18 there is shown a more preferred embodiment of a tissue specimen or organ removing system 120. The system 120 offers improvements over the system 20 from the standpoint of ease of use of the cutter, guide and bag. Thus, as can be seen in FIG. 12 the system 120 basically comprises a receptacle, e.g., a bag or pouch 122, or any other hollow flexible container, and an excising instrument 124. Like the system 20, the system 120 is configured for facilitating the removal of a large organ or tissue specimen 10 from within a space 12, e.g., the peritoneal cavity, in the body of a patient, via an opening or incision 14 to that space. The opening may be an incision 14, like shown in FIG. 12, or natural body opening, such as the vagina. In accordance with one aspect of this invention the incision/opening can be smaller than the organ/tissue specimen 10 to be removed.

The bag or pouch 122 is constructed similarly to the bag 22 and also in accordance with the teaching of our above identified patent application Ser. No. 14/986,890, except for the construction of its mouth portion. In particular, the bag or pouch 122 basically comprises a hollow member formed of any suitable flexible material, e.g., polyurethane film. However, unlike the bag 22, the bag 122 is constructed such that the perimeter the perimeter P at the opening of the bag 122, and which forms the mouth, does not include any support or roll-up ring. That said, the bag or pouch 122 can nevertheless be collapsed and rolled up, so that it can be inserted through a trocar (not shown) that extends through the incision 14 to a position within the peritoneal space 12, adjacent the tissue specimen or organ 10 to be removed. A grasper instrument of any suitable type (not shown) can be used to grasp the bag or pouch to ensure that its mouth 122A is open and to pull the open mouth to a desired position with respect to the tissue specimen or organ 10, which had previously been excised or freed from adjacent tissue. A second grasper instrument (not shown) can be used to move the excised tissue specimen or organ into and through the mouth of the bag or pouch, while holding the bag or pouch in place with the first grasper instrument. The mouth of the bag or pouch can then be pulled so that it is located outside of the patient's body as shown in FIGS. 12 and 13.

Once that mouth 122A of the bag 122 has been "extra-corporealized" (i.e., positioned outside of the patient's body), a tissue retractor 101, such as the one disclosed in U.S. Pat. No. 6,382,211 (Crook), whose entire disclosure is incorporated by reference herein, is positioned within the mouth 122A of the bag 122 and pushed through the incision/natural body opening 14 to retract the incision/opening 14, as shown in FIG. 12. This action provides a port through which the instrument 124 can be inserted. The retractor 101 includes a resilient or elastic sidewall 101A which engages the periphery of the excising instrument 124 when that instrument is inserted into the bag or pouch through the retractor 101. That action forms a fluid tight seal or interface between the retractor's sidewall 101A and the excising instrument, while also maintaining the seal of the insufflated peritoneal space during use of the instrument 124.

The excising instrument 124 will be described in detail shortly and is similar in most respects to the construction and operation of the excising instrument 24 of the system 20. Suffice it for now to state that the instrument 124 is constructed to be operated in such a manner that a rotatable cutting blade of the instrument engages peripheral portions of the tissue specimen or organ, while some pulling device, e.g., a grasper 16, pulls on that tissue specimen or organ. That pulling action rotates the tissue specimen or organ within the bag, whereupon the engagement of the rotating cutting blade with the rotating tissue specimen or organ tangentially cuts away portions of the tissue specimen or organ, somewhat like the peeling of the skin of an apple. Continued pulling on the tangentially cut portions of the tissue specimen or organ by the pulling device removes those portions from the body of the patient, while the bag traps any debris, cells, etc., produced during the cutting action within the bag. After the entire tissue specimen or organ has been excised and removed from within the bag, the instrument can be withdrawn from the bag, and the bag can then be removed from the patient's body through the incision 14.

Turning now to FIGS. 14-18 the details of the excising instrument 124 will now be described. As can be seen the instrument 124 basically comprises a cutter 128 and a guide 130. The cutter 128 is rotatably mounted within the guide 130 and comprises an assembly of six components, namely, a tubular cutting member 132, a handle or dial 134, a counter pressure member 136, washers 138A and 138B, and a sealing member 139. The tubular cutting member 132 is an elongated tube having a distal end 132A, a proximal end 132B, and a central passageway 132C extending between those ends. A central longitudinal axis X extends down the center of the passageway 132C and serves as the axis about which the cutter is rotated. The tubular cutting member 132 is of circular profile, with the distal end 132A being in the form of a sharp cutting edge or blade. The tubular cutting member 34 can be formed of any suitable material, e.g., hardened stainless steel.

Figure 14:
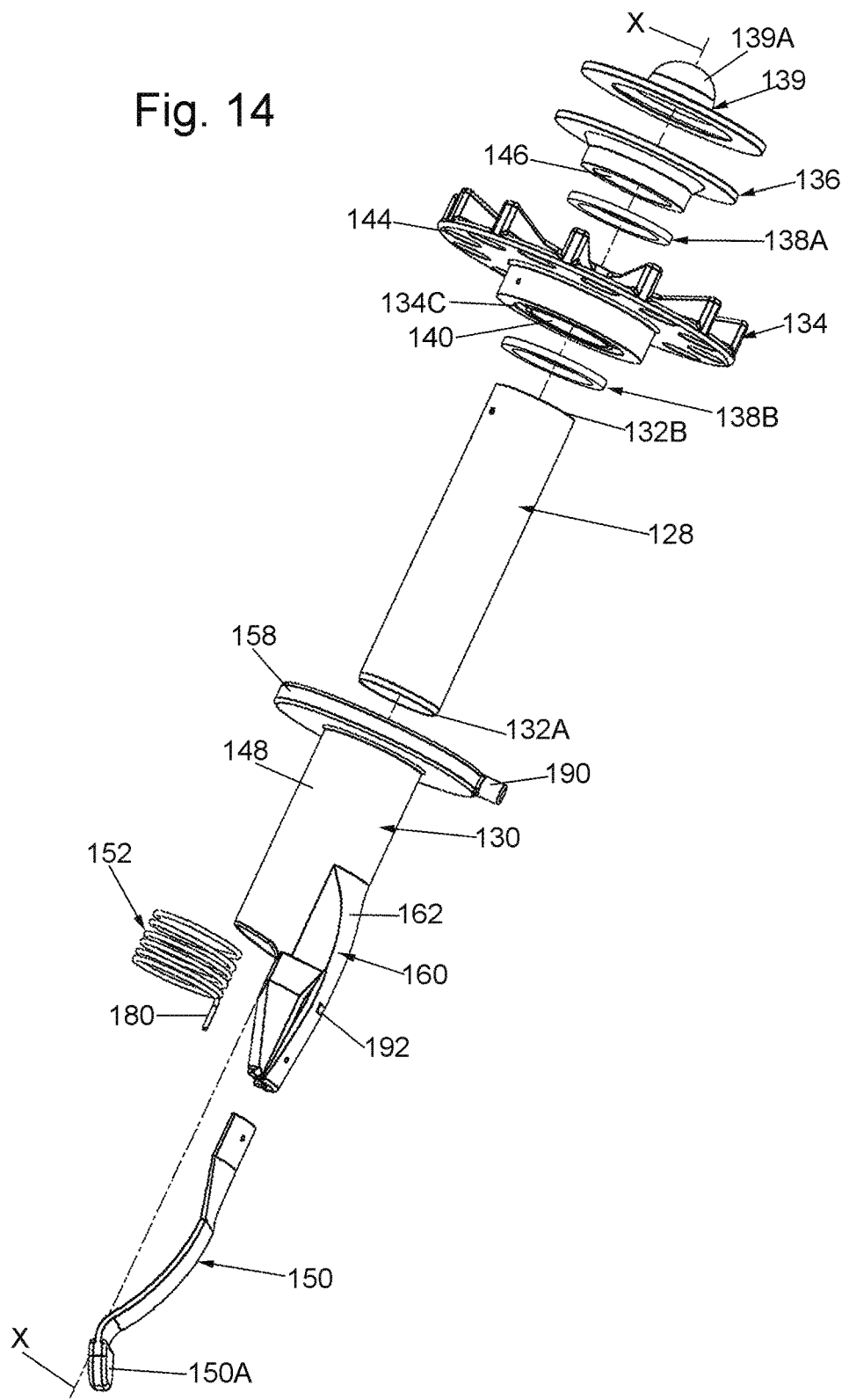
FIG. 14 is an exploded view of the excising instrument of FIG. 12 showing its back side.
Figure 15:
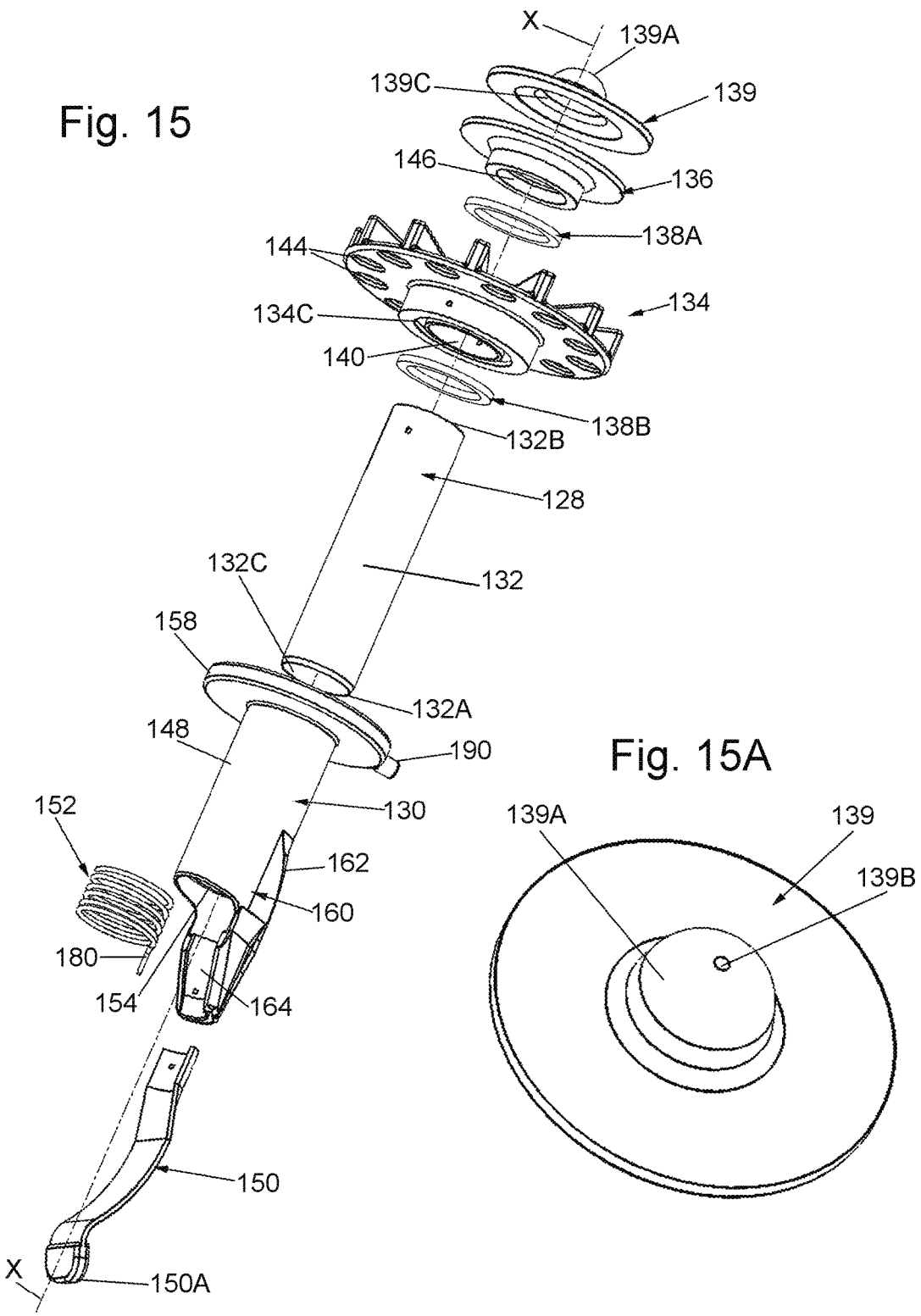
FIG. 15 is an exploded view of the excising instrument of FIG. 12 showing its front side.
Figure 16:
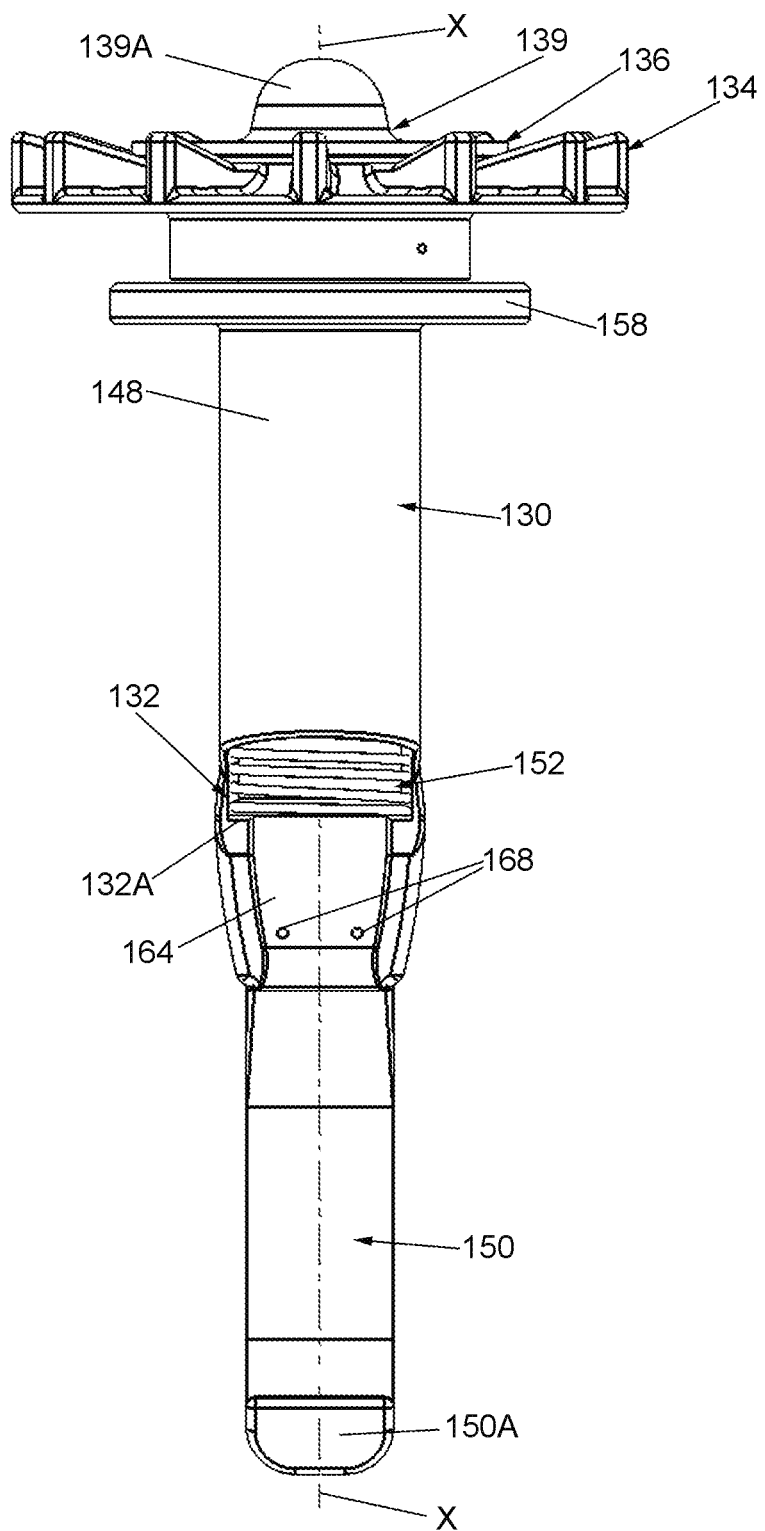
FIG. 16 is a front elevation view of the front side of the excising instrument of FIG. 12.

The handle 134 of the cutter 128 is in the form of an annular disk-like member or dial that can be formed of any suitable material, e.g., a plastic such as ABS or polycarbonate. The dial includes a central hole 140 through which the proximal end 132A of the tubular cutting member 132 extends and to which it is fixedly secured. The top surface of the handle or dial 134 includes an annular recess 142 (FIGS. 12 and 18) which is concentric with the center hole 140 (FIGS. 14 and 15). The annular recess 142 is configured to receive the washer 138A. Similarly, another annular recess 138C (FIGS. 14, 15 and 18) on the underside of the handle or dial 134 is configured to receive the second washer 138B therein. The washers 138A and 138B act as low friction bearing surfaces to allow the handle 134 to be turned easily, while also acting as seals. The handle or dial 134 also includes a plurality of apertures or openings 144 (FIGS. 14 and 15) that are equidistantly spaced from one another and located adjacent the outer periphery of the handle or dial 134. Each of the openings in the handle/dial 134 is configured to receive a finger of a user to effect the rotation of the cutter 128 with respect to the guide 130, as will be described later.

The counter-pressure applying member 136 is provided to apply a counter pressure on the instrument while the tissue that is being cut by the cutter is pulled through the cutter, as will be described later. The counter pressure applying member 136 can be formed of any suitable material, e.g., a plastic such as ABS or polycarbonate, and basically comprises a disk-like body of circular profile having a central opening 146 (FIGS. 14 and 15). The central opening 146 is configured to receive the proximal end 132B of the tubular cutting member 132.

The washers 138A and 138B are preferably formed of any suitable low friction material, such as Teflon®. As mentioned above, the washers are configured to be received within respective annular recesses 142 and 138C in the handle or dial 134. This feature enables one to readily rotate the handle or dial 134 to thereby rotate the tubular cutting member 132, with respect to the counter-pressure applying member 136, while one applies downward pressure on the counter-pressure applying member 136 during use of the instrument. That procedure will be described later.

The sealing member 139 may also be formed of any suitable material, e.g., a plastic such as ABS or polycarbonate, and basically comprises a disk-like body of circular profile and a central passageway 139C (FIGS. 14 and 15). The sealing member 139 is secured to the counter-pressure applying member 136 by any suitable means, e.g., ultrasonic bonding. As best seen in FIG. 15A the sealing member 139 comprises a pliable, elastomeric material dome 139A (e.g., a rubber diaphragm) having a central hole or aperture 139B at the top thereof. The aperture 139B allows the passage of an instrument (e.g., the grasper 16 shown in FIGS. 12 and 13) through it into the interior of the cutter 128. The dome feature 139A provides the surgeon with the ability to manipulate the grasper 16 or other instrument extending through the sealing member and into the interior passageway of the cutter, while forming a seal about the periphery of that grasper/instrument. This feature seals or isolates the interior of the bag 122 from the ambient atmosphere, while still enabling the surgeon to manipulate the grasper 16 or other instrument within the cutter 128. Moreover, the sealing of the dome 139A about the periphery of the grasper 16 or other instrument enables the surgeon to inflate the bag 122, if needed to facilitate the positioning of the instrument 120 with respect to the tissue or organ 10, as will be described later. Further still, the unit of the counter pressure applying member 136 and domed sealing member 139 are detachably coupled to the handle or dial 134 so that the user can lift the domed sealing member and the pressure applying member unit off of the handle or dial 134 to enable visualization of the grasper tip and specimen by looking down the central passageway 132C in the annular cutter 132.

Referring now to FIGS. 14, 15 and 18, the details of the guide 130 will now be described. Thus, as can be seen the guide 130 basically comprises an assembly of a guide body 148, a passer 150, and a retractable sleeve 152, which can be of any suitable construction. In the exemplary embodiment shown it is in the form of a helical compression spring. The guide body 148 can be formed of any suitable material, e.g., a plastic, such as ABS or polycarbonate, and is a generally tubular member having a central passageway 154 (FIG. 18) extending fully through it. The passageway 154 is centered about a central longitudinal axis X and is of an internal diameter just slightly larger than the external diameter of the tubular cutter member 132 to receive the tubular cutter member therein. The proximal end of the guide body 148 is in the form of an outwardly extending shoulder or flange 158. The lower section or distal end of the guide body 148 terminates in a thickened wall 160 that projects downward. The projecting wall 160 has an arcuate outer surface 162 and an inner surface 164. The inner surface 164 is configured to receive portions of the passer 150 to fixedly mount the passer 150 thereon. To that end, two apertures 168 extend through the wall 160. The apertures 168 are configured to receive respective pins (not shown) extending through respective tines (to be described shortly) making up a portion of the passer 150. The inner surface 164 of the guide member at the location of the thickened wall 160 includes an elongated annular recess or channel 170 (FIG. 18) extending parallel to and centered about the longitudinal central axis X. The channel 170 is configured to receive a portion of the retractable sleeve, e.g., spring, 152.

The passer 150 is best seen in FIGS. 14, 15 and 18, and basically comprises a curved elongated tongue-shaped member designed to pass around a portion of the excised tissue specimen or organ 10 between that tissue specimen or organ and the contiguous inner surface of the wall of the bag or pouch 122. The passer preferably is made of a material, e.g., nylon, which exhibits good shape retention properties during use. In particular, it has been determined that is necessary, occasionally, to reposition the guide body 130 within the bag 122. In order to accomplish this, the guide member 130 and passer 150 are removed completely from the incision 14 and typically rotated 90° or 180° and then reinserted. In order to facilitate this removal and reinsertion, repeatedly, while permitting the passer 150 to retain its shape during use, the passer 150 is formed of a shape retaining material, e.g., nylon, to retain the arcuate or curved shape shown in the various figures. In the interest of safety the distal or free end 150A of the passer is flared and rounded to make it atraumatic. Like the passer 50 of the system 20, the passer 150 of the system 120 is designed so that when the instrument 124 is in place within the bag or pouch it is located between the inner surface of the bag or pouch 122 and the outer surface of the excised tissue specimen or organ 10. That action effectively cradles and supports the tissue specimen or organ during use the operation of the system 120. Moreover, the arcuate nature of the passer 150 ensures that when the instrument 124 is inserted into the bag or pouch the cutter 128 will be oriented in a desired somewhat angular orientation to engage a peripheral portion of the tissue specimen or organ, like shown in FIG. 12. In particular, the passer 150 serves the purpose of aligning the cutter at the perimeter of the tissue specimen or organ in a generally tangential orientation relative to the specimen or organ. This is important as ideally one wants the tissue specimen or organ to rotate to the extent possible (so that it is cut much like peeling an apple in a continuous strip). If the cutter is not oriented properly it could core into the middle of the tissue specimen or organ, thereby jamming the instrument 124 with tissue.

The retractable sleeve, e.g., spring 152, is provided to protect the bag or pouch from being cut by the cutter. As mentioned earlier, the exemplary embodiment the retractable sleeve 152 comprises a helical compression spring. The inner diameter of the helical spring is just slightly greater than the outer diameter of the tubular cutter member 132 to accommodate the distal end portion of the tubular cutter member 132 within it. One end of the spring 152 is the form of a linear extension 180 that extends parallel to the axis X and which is located in the annular channel 170 at the distal end of the guide member 130. The spring 152 is normally biased such that at least one coil at the lower or free end of the spring extends beyond the blade 132A of the cutter 132, as best seen in FIGS. 12 and 13 thereby covering the blade 132A. This feature is of considerable importance in the interest of safety. In particular, the retractable sleeve 152 serves to cover the cutter's blade edge 132A so that the flexible film making up the bag or pouch 122 does not come into contact with the blade edge in scenarios where the blade edge might not be surrounded by tissue and the differential pressure in the peritoneal space 12 might be inclined to push the film of the bag or pouch 122 into the blade edge, whereupon the bag or pouch may be cut or otherwise damaged by the blade edge. Being a compression spring, it is normally biased in its extended position, such that the blade edge 132A is not exposed.

The system 120 has another feature over the system 20 described above. In particular, the instrument 124 includes an inflation feature that permits the instrument 124 to inflate the bag or pouch 122 during use. In this regard it has been determined that during use of the excising instrument 24 of the system 20, the bag or pouch 22 may conform to the specimen or organ 10 positioned therein due to the differential pressure from the peritoneal space. That action may make it difficult, in some circumstances, to remove the specimen or organ 10. To overcome this tendency, the excising instrument 124 comprises an inflation passageway 194 that permits the surgeon to inflate the bag or pouch 122 with a gas through the instrument 124 during use. The inflation passageway extends down the guide member 130 from an inlet port 190 located in the flange 158 at the proximal end of the guide member to an outlet port 192 located at the distal end of the guide member. In particular, the extending shoulder/flange 158 of the instrument 124 includes a tubular inlet port 190 configured for coupling to a gas pressure source PS (not shown), e.g., an inflation bulb/pump such as disclosed in U.S. Patent Publication No. 2014/0148731 (Radl, et al.), whose disclosure is incorporated by reference herein or to any other pressure source or insufflator. In the system shown in FIGS. 12 and 13 the pressure source is coupled to the excising instrument 124 via a flexible pressure line or conduit PL that is connected to the inlet port 190. The pressure of the gas provided from the pressure source is preferably set to a level that is several mm Hg greater than the pressure provided by the insufflator that is used to insufflate the peritoneal cavity. That action ensures that the bag or pouch is inflated notwithstanding the pressure applied to the outer surface of the bag or pouch by the insufflated peritoneal space. The gas provided to the inlet port 190 from the pressure source is directed through the guide 130 via a longitudinally extending internal passageway 194 (FIGS. 12, 13 and 18) in the sidewall of the guide 130 and out through the outlet port 192 located at the distal end of the guide body 148, in the projecting wall 160. Since the inlet port 190 is located on the shoulder/flange 158 it remains external to the patient so that it can readily be coupled via the pressure line PL to the pressure source.

As shown in FIGS. 12 and 13, and as will be appreciated by those skilled in the art, the sides of the incision/natural opening 14 press against the sidewall of the retractor, which in turn sealing engages the periphery of the instrument's guide member 130, thereby enabling the bag or pouch to be inflated by the pressurized gas 196 (FIG. 13) exiting the outlet port 192, and without that gas leaking out of the bag or pouch via the interface between the retractor sidewall and the excising instrument.

Turning now to FIG. 12, use of the instrument 124 is as follows: After the bag or pouch 122 has been introduced into the body of the patient and the tissue specimen or organ 10 located within the bag or pouch 122 and the mouth portion 122C of the bag 122 has been extra-corporealized" (positioned outside of the patient's body), the retractor 101 is positioned within the mouth 122A of the bag 122 and pushed through the incision/natural body opening 14 to retract the incision/opening 14, as shown in FIG. 12. The distal end of the instrument is then introduced through the mouth of the bag and through the retractor and advanced until the passer is in a position like that shown in FIG. 12, where it cradles the existed tissue specimen or organ 10. The resilient sidewall 101A of the retractor 101 makes a fluid tight seal with the periphery of the guide member 130. The shoulder portion 158 of the guide member 130 prevents it from being inserted too far into the bag or pouch. The cutter 128 is then inserted into the guide member 130. In particular, the tubular cutter member 132 is extended through the passageway 154 in the guide member and through the retractable sleeve 52, until the blade 132A contacts the tissue specimen or organ 10, with the cutter 128 being aligned at the perimeter of the tissue specimen or organ in a generally tangential orientation. After the cutter 128 and guide 130 are positioned, the sealing member 139 and the counter pressure member 136, which are separate from the cutter 128, are held away from the cutter 128. A tissue grasper instrument or device 16 is then advanced through the aperture 139A in the sealing member 139. The surgeon then holds the grasper 16 with the sealing member 139 and the counter pressure member 136 attached to it. This way, the surgeon can look down into the cutter 128 and see the tissue while applying the grasper 16 securely to the tissue specimen or organ 10. Once the tissue specimen or organ 10 is securely grasped, the sealing member 139 and the counter pressure member 136 are slid down the grasper 16 as a unit into engagement with the cutter 128. Then the tissue specimen or organ 10 can be pulled in a proximal direction toward the blade 132A like shown in FIG. 12. The cutter 132 is then rotated or spun using its handle or dial 134, while pulling on the tissue specimen or organ with the grasper 16. As the tissue specimen or organ 10 s pulled by the grasper 16, it tends to want to force the cutter 128 out of the bag or pouch 122. In order to counter this force, a force is applied by hand to the sealing member 139 and the counter-pressure member 136. In particular, at the same time that the handle or dial 134 is rotated, a force is applied to the lid 139 and the counter-pressure member 136 so that the action of pulling on the tissue specimen or organ 10 with the grasper 16 does not force the guide 130 and cutter 132 out of the mouth 122A of the bag or pouch 122. Typically, one person pulls on the tissue specimen or organ 10 with the grasper 16 while pushing on the sealing member 139 and the counter-pressure member 136, thereby holding them stationary as a unit, and a second person turns the dial 134 of the cutter 128 with respect to the unit of the stationary sealing member 139 and counter-pressure member 136. Inasmuch as the washers 138A and 138B are formed of a low friction material, the dial 134 can be rotated easily with respect to the unit of the sealing member 139 and counter-pressure member 136.

The downwardly projecting wall 160 serves as a blade-edge-blocking member adjoining the passer 150 and blocks about 30-40% of the blade 132A. This helps to keep the blade 132A in a tangential orientation relative to the tissue specimen or organ 10. It also prevents tissue that is cut from the tissue specimen or organ from completely filling the passageway 132C of the cutter 128, which could result in "packing" of the cutter tube 132 making it harder to rotate and extract tissue.

As mentioned earlier, the retractable sleeve, e.g., spring 152, covers the blade edge 132A so that the film of the bag or pouch 122 does not come into contact with the blade edge 132A in scenarios where the blade 132A might not be surrounded by tissue and the differential pressure in the peritoneal space might be inclined to push the film of the bag 122 into the blade edge 132A. The sleeve 152 is normally in its extended position such that the blade edge 132A is not exposed. When tissue specimen or organ 10 is grasped and pulled towards the blade edge 132A it causes the sleeve 152 to retract and the blade edge becomes exposed, allowing it to cut into the tissue specimen or organ. If there is no tissue specimen or organ 10 present, the sleeve 152 natural bias will cause it return to its extended position. One advantage of using a spring as a sleeve 152 is that it pivots as well as moves linearly. This can be useful if tissue from the tissue specimen or organ 10 pulled into the passageway 132C of the cutter 128 from one side only. In this case the spring 152 would retract on the tissue side only and still remain extended on the opposite side.

If during the use of the instrument 124, as described above, it is determined that the bag or pouch 122 needs to be inflated to facilitate the positioning of the passer 150 between the inner surface of the bag or pouch 122 and the tissue specimen or organ 10 to facilitate the cutting of the tissue or organ by the cutter 128, the bag or pouch 122 can be inflated. To that end, the pressure source PS is activated to inflate the bag 122 as shown in FIG. 13. It should be noted, depending on the type of pressure source, e.g., an inflation bulb/pump or a continuous pressure source (e.g., an insufflator that is continuously running), the bag or pouch 122 can either be intermittently inflated or continuously inflated, respectively. Thus, if the bulb/pump is used, the bag or pouch 122 will remain inflated only as long as one pumps the bulb. This action may be sufficient to just inflate the bag 122 periodically to allow the surgeon to manipulate the excised tissue or organ 10 within the bag 122. If not, the bag or pouch can be inflated continuously.

It should be pointed out at this juncture that the system 120 of FIG. 12 may not be 100% fluid-tight. In particular, it is likely that there will be some leaks between the bag or pouch and the retractor and the retractor and the guide due to wrinkles in the material making up the bag or pouch. Thus, to inflate the bag or pouch the inflation source should be configured to be able to overcome such leakage to maintain the bag or pouch in its inflated state. In the case where the inflation source is provided by a hand bulb, that bulb is squeezed intermittently, whereupon the inflated state is only temporarily maintained.

In any case, as described with reference to FIG. 12, any type of tissue grasper instrument or device 16 can be inserted through the aperture 139B in the pliable dome 139B and passageway 139C of the sealing member 139 and into the passageway 132C of the tubular cutter member 132 so that it can grasp and the tissue specimen or organ 10, whereupon the tissue specimen or organ 10 can be pulled in a proximal direction toward the blade edge 132A like shown in FIG. 13. The cutter 132 is then rotated or spun using its handle or dial 134, while pulling on the tissue specimen or organ with the grasper 16. As the tissue specimen or organ 10 s pulled by the grasper 16, it tends to want to force the cutter 128 out of the bag or pouch 122. In order to counter this force, a force is applied by hand to the sealing member 139 and the counter-pressure member 136. In particular, at the same time that the handle or dial 134 is rotated, a force is applied to the lid 139 and the counter-pressure member 136 so that the action of pulling on the tissue specimen or organ 10 with the grasper 16 does not force the guide 130 and cutter 132 out of the mouth 122C of the bag or pouch 122.

Further still, the counter pressure washer and domed seal of excising instrument are detachably coupled to the dial so that the user can lift it off to enable visualization of the grasper tip and specimen by looking down into the annular cutter.

As also described with reference to FIG. 12, the downwardly projecting wall 160 serves as a blade-edge-blocking member adjoining the passer 150. That wall blocks about 30-40% of the blade edge 132C. This helps to keep the blade edge 132A in a tangential orientation relative to the tissue specimen or organ 10. It also prevents tissue that is cut from the tissue specimen or organ from packing the cutter and thus making it harder to rotate and extract tissue. The retractable sleeve, e.g., spring 152, covers the blade edge 132A, as described above so that the film of the bag or pouch 122 does not come into contact with the blade edge 132A in scenarios where the blade 132A might not be surrounded by tissue and the differential pressure in the peritoneal space might be inclined to push the film of the bag 122 into the blade edge 132A.

In accordance with one preferred embodiment to the invention the film making up the bag or pouch 122 is 0.006 inches thick and has a durometer of approximately 90 shore A and a 100% modulus of 1,700 psi. The combination of the film thickness and material properties make the film stiff enough such that the peritoneal insufflation pressure does not cause the film to conform around the spring/shield 152 and into contact with the blade edge 132A.

It should be pointed out at this juncture that the systems and methods of use as described above are merely exemplary. Thus, other systems/devices can be constructed in accordance with the teachings of this invention and other methods of removing an organ or tissue specimen from the body of a patient through an incision or natural body opening can be accomplished, as well. For example, the various components of the systems 20 and 120, e.g., bags or pouches 22 and 122, excising instruments 24 and 124, and tissue retractor 101 can be combined in different ways to form alternative systems and alternative methods to the exemplary systems and methods described above. Moreover, the tongue/passers 50 and 150 need not be arcuate, but can also be straight. In that case, inserting such a passer 150 into the bag or pouch 122 between the tissue specimen or organ 10 and the inner surface of the film making up the bag or pouch 122 will cause it to flex into a curved configuration as it is advanced along the perimeter of the specimen.

Without further elaboration the foregoing will so fully illustrate our invention that others may, by applying current or future knowledge, adopt the same for use under various conditions of service.

We claim:

1. An excising instrument for use in a system for removing a tissue specimen or organ from the body of a patient through an opening in the patient's body, the tissue specimen or organ being located within a flexible bag or pouch located within an interior space in the body of the patient and with a mouth portion of the bag or pouch being located outside of the body of the patient, said instrument comprising:

a guide member having a distal end portion configured for introduction through said mouth portion of the bag or pouch to a position adjacent the tissue specimen or organ, a proximal end portion configured for location outside the body of the patient, and a longitudinal axis extending between said distal end portion and said proximal end portion, said guide member comprising an elongated passer member extending downward from said distal end portion on one side of said longitudinal axis and curving to an opposite side of said longitudinal axis, said passer member being configured for location interposed between the bag or pouch and the tissue specimen or organ to curve under a first peripherally located portion of the tissue specimen or organ to cradle and support the first peripherally located portion of the tissue specimen or organ thereon; and a cutter mounted for rotation within said guide member about said longitudinal axis, said cutter comprising a tubular member having a central passageway and a distal end in the form of an annular cutting blade, said annular cutting blade being configured to be brought into engagement with a second peripherally located portion of the tissue specimen or organ to cut into the second peripherally located portion as the first peripherally located portion of the tissue specimen or organ is cradled and supported by said elongated arcuate passer member and said cutter is rotated about said longitudinal axis to produce a tangentially cut peripheral portion, whereupon the tangentially cut peripheral portion will be in communication with said central passageway, said central passageway being configured for receipt of a pulling device extended therethrough to pull the tangentially cut peripheral portion into and through said central passageway in the proximal direction, whereupon said tangentially cut peripheral portion is withdrawn out of the body of the patient.

2. The instrument of claim 1 wherein said guide member additionally comprises a blade blocking member connected to said distal end portion of said guide member and interposed between said annular cutting blade and the bag or pouch.

3. The instrument of claim 1 wherein said elongated arcuate passer member is tongue-shaped.

4. The instrument of claim 3 wherein said elongated arcuate passer member comprises a material for maintaining its shape during use.

5. The instrument of claim 4 wherein said material is nylon.

6. The instrument of claim 1 wherein said cutter additionally comprising a handle, said handle being located outside of the body of the patient at said proximally located portion of said guide member, said handle being configured to be rotated about said longitudinal axis to effect the rotation of said annular cutting blade about said longitudinal axis.

7. The instrument of claim 6 wherein said handle comprises a disk-like member of circular profile with plural openings located adjacent the periphery thereof.

8. The instrument of claim 1 additionally comprising a retractable sleeve configured to be automatically extended from a retracted position to an extended position, said sleeve when in said extended position covering said annular cutting blade so that said annular cutting blade does not engage the bag or pouch if the annular cutting blade is not surrounded by portions of the tissue specimen or organ.

9. The instrument of claim 8 wherein said sleeve comprises a helical compression spring.

10. The instrument of claim 1 additionally comprising a counter pressure member configured to have a counter-force applied thereto as the pulling device pulls the tangentially cut peripheral portion into and through said central passageway in the proximal direction.

11. The instrument of claim 10 wherein said counter pressure member is a disk-like member.

12. The instrument of claim 1 wherein said guide member comprises a gas passageway, configured for coupling to a source of inflation gas, for enabling the bag or pouch to be inflated so that the tissue specimen or organ can be readily moved or positioned within the bag or pouch.

13. The instrument of claim 12 wherein said gas passageway extends through a portion of said guide member between an inlet port and an outlet port, said outlet port being located within the bag or pouch when said guide member is inserted therein, said inlet port being configured to be coupled to the source of inflation gas located outside the body of the patient.

14. The instrument of claim 12 wherein said source of inflation gas comprises a compressible bulb.

15. The instrument of claim 12 comprising a sealing member configured to engage a portion of the pulling device to prevent egress of said gas through an interface between said sealing member and said portion of the pulling device, while enabling the pulling device to pull said tangentially cut peripheral portion out of the body of the patient.

16. The excising instrument of claim 15 wherein said sealing member comprises a pliable dome having an opening to allow passage of the pulling device therethrough while maintaining a pressurized environment with the body of the patient.

17. A tissue specimen or organ removal system comprising the instrument of claim 1 and the flexible bag or pouch.

18. The system of claim 17 additionally comprising a retractor configured for insertion into the mouth portion of said bag or pouch to enable said excising instrument to be introduced therethrough.

19. The system of claim 18 wherein said retractor includes a sidewall configured for engaging a portion of the periphery of said excising instrument to form a fluid-tight seal therebetween.

20. The system of claim 17 wherein said flexible bag or pouch includes a ring located adjacent said mouth of said bag or pouch and about which portions of said bag or pouch can be rolled up.

* * * * *